(12) United States Patent
Iida et al.

(10) Patent No.: US 7,058,244 B2
(45) Date of Patent: Jun. 6, 2006

(54) MICROCHIP, METHOD OF MANUFACTURING MICROCHIP, AND METHOD OF DETECTING COMPOSITIONS

(75) Inventors: Kazuhiro Iida, Tokyo (JP); Masatoshi Tokushima, Tokyo (JP); Tsuyoshi Shimoda, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 11/049,357

(22) Filed: Feb. 1, 2005

(65) Prior Publication Data

US 2005/0175273 A1 Aug. 11, 2005

Related U.S. Application Data

(63) Continuation of application No. PCT/JP03/09720, filed on Jul. 31, 2003.

(30) Foreign Application Priority Data

Aug. 2, 2002 (JP) ............................. 2002-226681

(51) Int. Cl.
*G02B 6/00* (2006.01)
*H01L 21/00* (2006.01)

(52) U.S. Cl. .................... 385/12; 385/14; 385/125; 385/129; 385/130; 385/131; 385/132; 438/29; 438/31

(58) Field of Classification Search ............... 385/12, 385/14, 129, 130, 131, 132, 125, 126; 438/29, 438/31

See application file for complete search history.

(56) References Cited

U.S. PATENT DOCUMENTS

| 5,173,747 A | * | 12/1992 | Boiarski et al. | ............ 356/481 |
| 6,194,900 B1 | * | 2/2001 | Freeman et al. | ............ 324/321 |
| 6,438,279 B1 | * | 8/2002 | Craighead et al. | ............ 385/12 |
| 6,753,200 B1 | * | 6/2004 | Craighead et al. | ............ 438/48 |
| 6,917,726 B1 | * | 7/2005 | Levene et al. | ................ 385/12 |
| 2003/0017079 A1 | | 1/2003 | Hahn et al. | |
| 2003/0169987 A1 | * | 9/2003 | Eggleton et al. | ............ 385/125 |

FOREIGN PATENT DOCUMENTS

| DE | 199 05 983 | 10/2000 |
| JP | 62-108858 | 7/1987 |
| JP | 1-233345 | 9/1989 |
| JP | 9-15205 | 1/1997 |
| JP | 9-236540 | 9/1997 |
| JP | 9-288090 | 11/1997 |
| JP | 2000-304686 | 11/2000 |
| JP | 2002-98637 | 4/2002 |
| JP | 2002-159285 | 6/2002 |
| JP | 2002-162346 | 6/2002 |
| JP | 2003-57477 | 2/2003 |
| JP | 2003-114193 | 4/2003 |
| JP | 2003-529076 | 9/2003 |
| WO | WO 01/73417 | 10/2001 |

* cited by examiner

*Primary Examiner*—Brian Healy
(74) *Attorney, Agent, or Firm*—Katten Muchin Rosenman LLP

(57) ABSTRACT

A microchip includes a clad layer having a channel through which a sample flows, and an optical waveguide formed within the clad layer and having a higher refractive index than the clad layer. The optical waveguide is formed to act on the channel optically. Thus, the sample flowing in the channel can be analyzed with high accuracy even in the microchip having a fine structure.

42 Claims, 22 Drawing Sheets

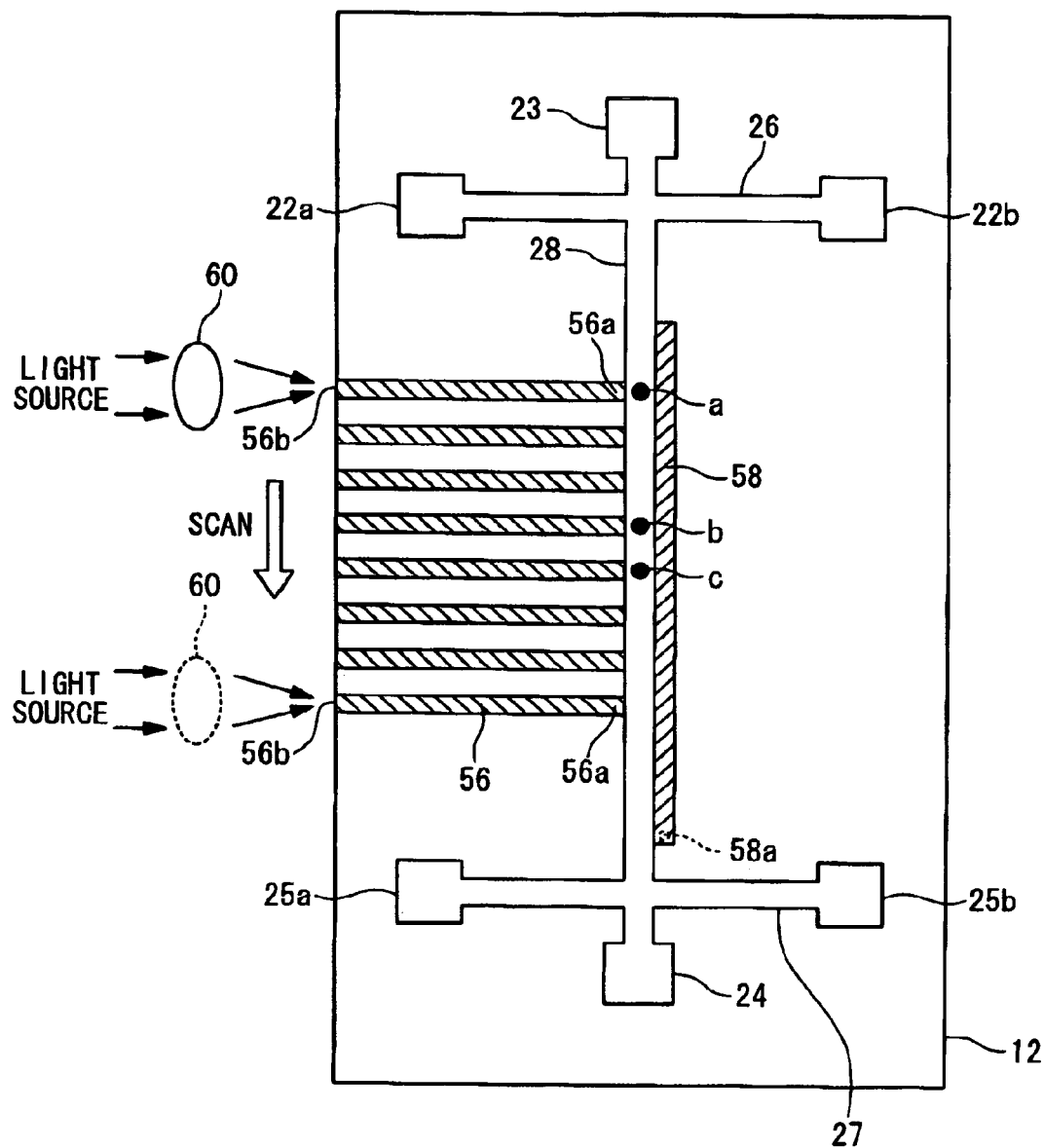

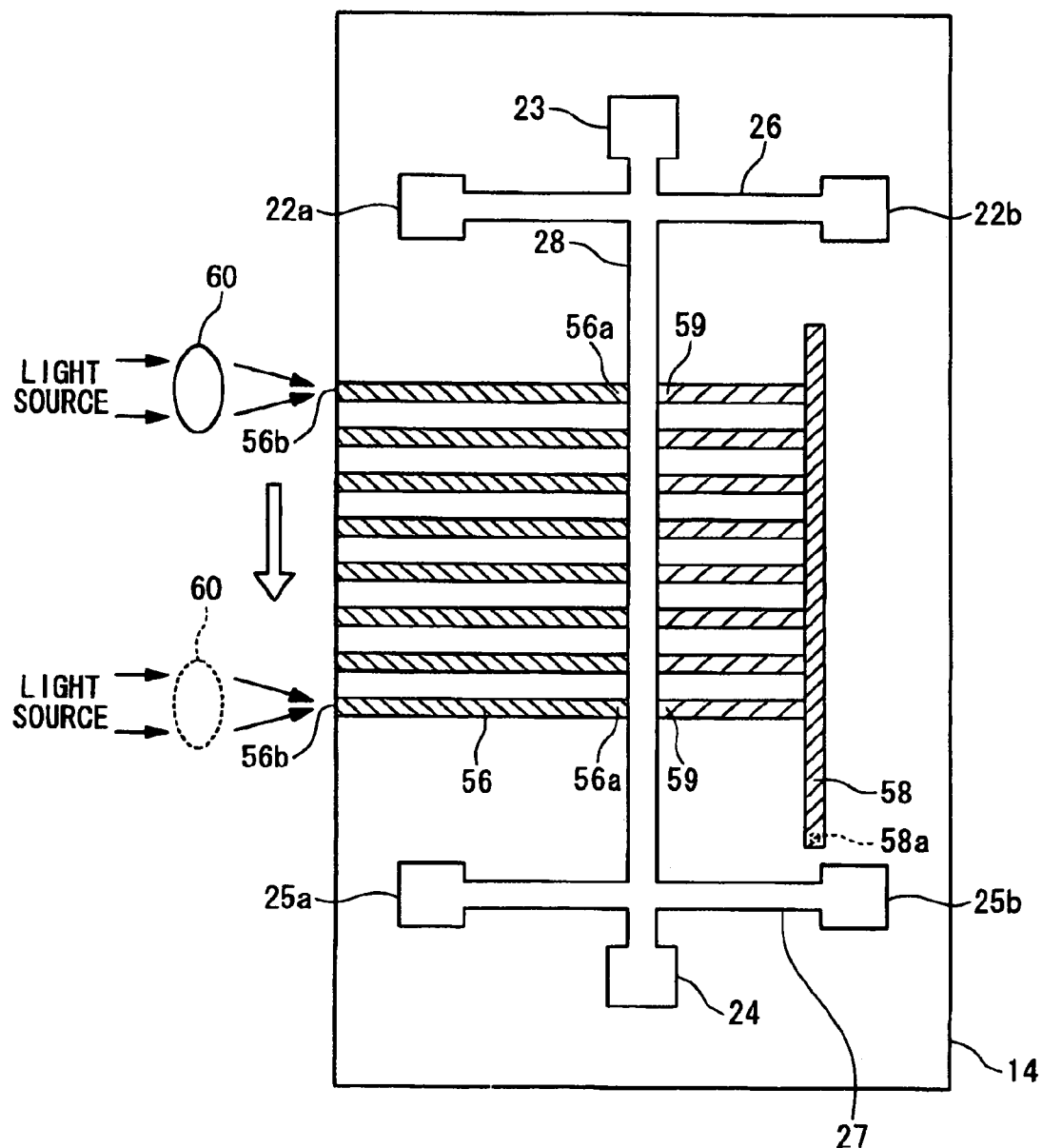

MICROCHIP, METHOD OF MANUFACTURING MICROCHIP, AND METHOD OF DETECTING COMPOSITIONS

This is a continuation of Application Ser. No PCT/JP03/09720, filed Jul. 31, 2003.

TECHNICAL FIELD

The present invention relates to a microchip, a method of manufacturing the microchip, and a method of detecting compositions.

BACKGROUND ART

There are strong needs for a microchip in a clinical investigation and a proteomics analysis. The microchip is used to separate biomolecule such as nucleic acid and protein and to analyze the separated sample. In such an analysis of the sample, a method for optically detecting very small amounts of separated samples has been utilized. As a technique for optically analyzing the samples, a transmission light technique and a diffuse reflection technique are known.

According to the diffuse reflection technique, a sample is analyzed by detecting a reflected light of a laser light which is irradiated to the sample. A densitometry apparatus described in Japanese Laid-open Patent Application No. 2002-98637 employs a laser emitting device, and measures density of suspensoid composition contained in target liquid under measurement by using the diffuse reflection technique. In this densitometry apparatus, a plurality of optical fibers for generating the laser light and a plurality of optical fibers for receiving the laser light are bundled to configure a sensor unit.

On the other hand, FIG. 1 is a diagram showing a densitometry apparatus using the transmission light technique which is described in Japanese Laid-open Utility Model Application No. Sho-62-108858. In this densitometry apparatus, a light emitted from a light source 221 is led to a liquid channel 201 through a light leading optical fiber bundle 222, the light emitted from an end section of the light leading optical fiber bundle 222 is entered to an end section of a light receiving optical fiber bundle 223 through the liquid channel 201, and concentration of a liquid flowing in the liquid channel is measured by a photo detector 224.

Also, an optical type analyzer described in Japanese Laid-open Patent Application No. Hei-1-233345 is characterized in that a light emitted from a light source is branched into a plurality of channels by a branching optical fiber. A light in one branched channel is entered to a reference light receiving device without entering to a sample. Lights in the other branched channels are entered to the sample, and the lights passing through the sample are entered to a sample light receiving device.

FIG. 2 is a diagram for showing a capillary electrophoresis apparatus described in Japanese Laid-open Patent Application No. Hei-9-288090. This capillary electrophoresis apparatus consists of a substrate 114 on which a channel 120 is formed, an optical fiber 108 embedded in the substrate 114, a light source 103 connected to the optical fiber 108, and a photo detector 135 connected to the substrate 114. In the apparatus, the photo detector 135 is provided above the channel 120 and a sample liquid is conducted into the channel under such a condition that the sample liquid is made dielectric by using fluorescent reagent. A sample excitation light is conducted from the light source 103 to the other end of the optical fiber 108, and the light derived from the optical fiber 108 is irradiated to a sensing section of the channel 120. The liquid sample receiving the light irradiation at the sensing section generates a fluorescent light, and the generated fluorescent light is entered to the photo detector 135.

According to a configuration in which the optical fiber bundles are arranged on both ends of the liquid channel as in the above-described densitometry apparatus described in the Japanese Laid-open Utility Model Application No. Sho-62-108858, it is difficult to align the light leading optical fiber bundle 222 with respect to the light receiving optical fiber bundle 223 correctly. As a result, there is such a risk that the concentration of the sample flowing through the channel cannot be measured in high precision.

In the case of the configuration in which the photo detector 135 is provided above the channel 120 as in the capillary electrophoresis apparatus described in the Japanese Laid-open Patent Application No. Hei-9-288090, it is difficult to secure the optical length enough to measure the absorption when the channel 120 is shallow and the observation is performed from the upper direction. Also, the optical fiber 108 is fixed by adhesive material to a groove 122 formed on the substrate 114. As a result, a process of fixing the optical fiber by using the adhesive material is necessary in addition to the positioning of the optical fiber. Thus, a method of manufacturing it becomes complex.

DISCLOSURE OF INVENTION

An object of the present invention is to provide a technique with which a sample flowing in a channel can be analyzed in high precision even in a microchip having a fine structure.

Another object of the present invention is to provide a technique with which compositions of a sample can be detected optically even in a very small channel formed on a plane.

Still another object of the present invention is to provide a technique with which a sufficient long optical length can be secured even in a shallow channel, and compositions of a sample flowing in the channel can be detected in high precision.

Still another object of the present invention is to simplify a structure of a microchip.

According the present invention, a microchip includes a clad layer having a channel through which a sample flows, and an optical waveguide formed within the clad layer and having a higher refractive index than the clad layer. The optical waveguide is formed to act on the channel optically, and it is thus possible to analyze compositions of the sample flowing through the channel. Here, acting optically means that a light propagating in the optical waveguide exercises an effect on the sample in the channel. Hence, the optical waveguide may be physically connected with the channel, or may be optically connected with the channel. Also, the optical waveguide may intersect with the channel, or may have a border with the channel.

The clad layer is made of a material whose refractive index is lower than that of a core layer (optical waveguide). The clad layer can includes clad layers which cover the bottom and the side of the core layer. Also, the clad layer can include a clad layer covering the top of the core layer as a component. In this case, the clad layer can include the channel on the surface of the clad layer covering the top of the core layer. With the configuration mentioned above, the core layer can be surrounded by the clad layer, and the core layer functions as an optical waveguide. It should be noted that the clad layer can have such a structure that the refractive index decreases gradually from the inner portion adjacent to the core layer to the outer portion.

According to the microchip of the present invention, the optical waveguide is formed in the clad layer. Therefore, it is not necessary to fix the optical waveguide to the clad layer by using adhesive material as in the conventional apparatus, which simplifies the configuration. Also, since the optical waveguide is formed within the clad layer in a planar form, fine processing is possible. Moreover, it is possible to simplify processes of manufacturing the microchip. Thus, the cost of manufacturing the microchip can be reduced. Furthermore, since the channel and the optical waveguide are formed in the clad layer, it is possible to make the sizes of the channel and the optical waveguide desired values with excellent controllability.

In a first aspect of the present invention, the optical waveguide intersects with the channel. In this case, a light led from one end of the optical waveguide passes through the channel and is came out from another end of the optical waveguide. With such a configuration, it is possible to detect compositions of the sample flowing in the channel on the basis of properties (such as intensity) of the light come out from the other end of the optical waveguide. The channel can be formed to divide the optical waveguide.

In the microchip of the present invention, the channel through which the sample flows and the optical waveguide provided to intersect with the channel are formed in the clad layer. Thus, it is not necessary to adjust the positions of them, and the one end of the optical waveguide formed across the channel can be used for leading the light and the other end can be used for receiving the light. Moreover, since the channel is formed in the clad layer, it is possible to form the channel with a desired size by using an existing technique which can perform the fine processing; for example, the etching.

The one end and the other end of the optical waveguide can be formed wider than another region of the optical waveguide. The optical waveguide can be formed wider at a boundary between the optical waveguide and the channel than another region of the optical waveguide. According to the configuration, the light entered to the channel from the one end of the optical waveguide formed across the channel is broadened. It is therefore possible to transmit the light in high precision from the one end to the other end across the channel, and to detect precisely the properties of the light which has passed through the sample flowing in the channel.

A plurality of optical waveguides can be formed within the clad layer. The plurality of optical waveguides can be formed apart from each other with a predetermined space, and can be formed substantially parallel to each other. With such a configuration, it is possible to detect almost simultaneously the properties of the lights which have passed through the samples at different positions in the channel, and to detect a separation pattern of the sample flowing in the channel.

A plurality of optical waveguides can be formed within the clad layer. The plurality of optical waveguides may include a plurality of light leading optical waveguides and a light receiving optical waveguide. The channel is formed between the plurality of light leading optical waveguides and the light receiving optical waveguide. The plurality of light leading optical waveguides are formed to lead the light at a plurality of different positions of the channel. The light receiving optical waveguide is formed to receive and output the light passing through each of the plurality of different positions. The plurality of light leading optical waveguides can be formed apart from each other and substantially perpendicular to the channel. The light receiving optical waveguide can be formed along the channel. In this case, a side surface along the channel and the opposite side surface of the light receiving optical waveguide can be made mirror surfaces. With this configuration, it is possible to transmit without loss in the light receiving optical waveguide the light entered to the light receiving optical waveguide through the channel, and to detect the compositions of the sample in high precision.

Also, a plurality of optical waveguides are formed within the clad layer, and the plurality of optical waveguides can include a plurality of light leading optical waveguides, a plurality of first light receiving optical waveguides as many as the plurality of light leading optical waveguides, and one second light receiving optical waveguide. The channel is formed between the plurality of light leading optical waveguides and the plurality of first light receiving optical waveguides. The plurality of light leading optical waveguides are formed to lead the light at a plurality of different positions of the channel. Each of the plurality of first light receiving optical waveguides is formed to receive the light passing through corresponding one of the plurality of different positions. The second light receiving optical waveguide is formed to receive and output the light propagating through each of the plurality of first light receiving optical waveguides. The plurality of light leading optical waveguides can be formed apart from each other and substantially perpendicular to the channel. The plurality of first light receiving optical waveguides can be formed apart from each other and substantially perpendicular to the channel. The second light receiving optical waveguide can be formed along the channel.

When the microchip includes the plurality of light leading optical waveguides as described above, it is possible to measure the time variation of the sample flowing through the channel by leading the light to the different positions of the channel with a predetermined time interval. Thus, when the microchip of the present invention is used for separating the compositions of the sample, it is possible to detect a timing of collecting the compositions under the separating process. In particular, it is possible to collect a target composition with certainty because the defluxion time of each composition can be predicted even in a case of separating and collecting unknown sample. Also, one of the plurality of optical waveguides can be used as a reference. Thus, it is possible to detect the compositions of the sample in high precision. In the microchip of the present invention, as mentioned above, the channel is formed to intersect with the optical waveguide in the clad layer in which the optical waveguide is formed. Therefore, it is not necessary to adjust the positions of them, and the one end of the optical waveguide formed across the channel can be used for leading the light and the other end can be used for receiving the light. Thus, the structure in which the plurality of optical waveguides are provided can be made with ease.

In the present invention, the optical waveguide does not necessarily intersect with the channel in the same plane. It is just necessary that the light entered from the one end of the optical waveguide is affected somehow by the sample flowing in the channel and is come out from the other end.

In a second aspect of the present invention, the optical waveguide is formed to share a border with the channel. It is enough that a part of the optical waveguide shares the order with the channel. The optical waveguide can include a region having the border with the channel, a light leading optical waveguide which leads a light to the region, and a light receiving optical waveguide which receives and outputs the light propagating through the region. With this configuration, an evanescent wave interacts with the sample at a region where the optical waveguide is in contact with the channel, which enables the detection of the compositions of the sample.

In a third aspect of the present invention, the optical waveguide serves as an interferometer. The optical waveguide has a light leading optical waveguide and a light receiving optical waveguide. The light leading optical waveguide branches into a first light leading optical waveguide and a second light leading optical waveguide in the clad layer. The light receiving optical waveguide branches into a first light receiving optical waveguide and a second light receiving optical waveguide in the clad layer. The channel is formed to pass through between the first light leading optical waveguide and the first light receiving optical waveguide and between the second light leading optical waveguide and the second light receiving optical waveguide. A first light led from the first light leading optical waveguide to the channel passes through the channel and enters into the first light receiving optical waveguide. A second light led from the second light leading optical waveguide to the channel passes through the channel and enters into the second light receiving optical waveguide. The first light and the second light are superposed in the light receiving optical waveguide. It is possible to detect a condition of the channel based on an appearance of the interference.

In a fourth aspect of the present invention, the optical waveguide has a light leading optical waveguide for leading the light to the channel, a light receiving optical waveguide for receiving and outputting the light passing through the channel, and a heating optical waveguide. The heating optical waveguide is formed upstream of the light leading optical waveguide with respect to the channel. The heating optical waveguide may be formed to intersect with the channel, or to share a border with the channel, or to surround the channel. A boundary surface between the heating optical waveguide and the channel is colored. The light led to the heating optical waveguide is absorbed by the colored boundary surface, and thus the sample in the channel which is in contact with the boundary surface is heated. Thus, the sample can be detected at an appropriate temperature without adding an external heater or an electric circuit. It is therefore possible to analyze the sample in high precision by using a simple microchip.

In a fifth aspect of the present invention, the detection of the sample is carried out by using a near-field light in a microchip having a fine channel. The optical waveguide is along the channel, and has a first optical waveguide and a second optical waveguide each of which has a surface exposed to the channel. The channel is formed between the first optical waveguide and the second optical waveguide. A width of the channel is comparative to molecule in the sample. The width of the channel can be no more than 50 nm. Alternatively, the microchip can further include a near-field probe. A tip of the near-field prove reaches within the channel. The optical waveguide is formed along the channel, and is exposed to the channel at a region facing the tip of the near-field probe. A surface of the optical waveguide may be processed to trap biomolecule in the sample. With this configuration, it is possible to optically detect the compositions of the sample even in a extremely small channel.

In the microchip of the present invention, the channel can include a separation region for separating the sample, and a detection region for detecting the sample separated in the separation region. The light is led from the optical waveguide to the channel in the detection region. The detection region is not necessarily aligned with the separation region, and may be connected to the separation region with an angle.

According to the microchip of the present invention, as described above, since the channel and the optical waveguide are formed in the clad layer, it is possible to make the sizes of the channel and the optical waveguide desired values with excellent controllability. For example, if the separation region is provided for the channel by a fine processing but the volume of the channel in the detection region is large, compositions separated in the separation region are mixed in the detection region. This causes fails in detecting the compositions in the sample and in collecting the separated compositions. According to the microchip of the present invention, the detection region can be also made fine. It is possible to detect in high precision the sample separated in the separation region with the separated condition, and hence to collect the separated compositions. According to the present invention, the size of the optical waveguide can be controlled appropriately, and thus the separation region can be formed by the nano-technology processing with the depth of the channel being, for example, 50 nm to 5 μm.

In the microchip of the present invention, the channel can be a groove formed on the clad layer. Since the channel is realized by the groove formed on the surface of the clad layer, it is possible to make the size (width, depth) of the channel desired values with excellent controllability. For example, the width of the channel can be made larger than the depth of the channel. As described above, the size of the channel can be controlled appropriately, the channel can be formed to have a depth required for separating the sample precisely and a width required for detecting the sample accurately. For example, the depth of the groove can be made not more than 5 μm. The lower limit of the depth of the groove is not limited in particular, but the depth can be made not less than 50 nm for example.

In the microchip of the present invention, the optical waveguide can be formed to be connectable with an optical fiber at an end section. The end section of the optical waveguide can be formed in a slope shape. Since the optical waveguide formed in the clad layer is connectable with the optical fiber, it is possible to transmit a light from an external light source and to an external detector through the optical fiber. Also, with such a configuration, it is possible to attach the optical fiber to and detach it from the microchip if necessary, and hence to simplify the configuration of the microchip. The optical fiber can be configured to be attachable to a side surface or a top surface of the microchip. In a microchip, a liquid reservoir used for supplying the sample and collecting the separated sample is often provided on a top side of the microchip. Therefore, when the top side of the microchip is configured to be connectable to an optical fiber, an operation plane can be set to the same plane. Thus, the usability of the microchip can be improved.

According to the present invention, a method of manufacturing a microchip includes the steps of: (a) forming a lower clad layer on a base substrate; (b) forming at least one groove on the lower clad layer; (c) forming an optical waveguide in the groove, the optical waveguide having a higher refractive index than the lower clad layer; (d) forming an upper clad layer over the lower clad layer to cover the optical waveguide, the upper clad layer having a lower refractive index than the optical waveguide; and (e) forming a channel to act on the optical waveguide optically.

In the (e) forming step, the channel may be formed to intersect with the optical waveguide. In the (e) forming step, the channel may be formed to divide the optical waveguide. In the (e) forming step, the channel may be formed to share a border with the optical waveguide.

In the (b) forming step, an end section of the groove may be formed to be a slope. In the (b) forming step, a reflective layer may be formed on a surface of the groove. In the (d) forming step, the upper clad layer may be formed such that it has a substantially equal refractive index to that of the lower clad layer.

The channel can be formed by the etching. It is also possible to form a channel by stamping out a film on which an optical waveguide is formed with a mold, and then to manufacture a clad layer in which the channel and the optical waveguide are formed by bonding the film and another film. A hydrophilicity process and an adhesion preventing process for preventing the sample from adhering to the channel can be performed on the surface of the channel as formed above. As the adhesion preventing process, a material having a similar structure to phosphatide constituting a cell wall or fluorocarbon polymer can be applied to the side wall of the channel.

According to the present invention, a method of detecting compositions in a microchip is provided. The microchip includes a clad layer having a channel, and a plurality of light leading optical waveguides and a plurality of light receiving optical waveguides which are formed in the clad layer to intersect with the channel. The method includes the steps of: (A) flowing a sample in the channel; (B) inputting a light to a plurality of positions of the channel almost simultaneously through the plurality of light leading optical waveguides; (C) the light passing through the sample at the plurality of positions; (D) receiving through respective of the plurality of light receiving optical waveguides the light passing through the plurality of positions; and (E) analyzing the sample flowing in the channel based on properties of the received light.

Here, the inputting almost simultaneously may be realized by inputting the lights to the plurality of optical waveguides substantially simultaneously by using a plurality of light sources, or realized by inputting the light to the plurality of optical waveguides substantially simultaneously by scanning a light from one light source. The properties of light are light profiles such as an intensity profile and a wavelength profile. According to the method, the lights are supplied from the plurality of optical waveguides almost simultaneously. Since the lights passing through the channel can be obtained in relationship to the positions of the channel, it is possible to detect a separation pattern of the compositions of the sample. Therefore, when the microchip of the present invention is used for separating the compositions of the sample, it is possible to detect a timing of collecting the compositions under the separating process. In particular, it is possible to collect a target composition with certainty because the defluxion time of each composition can be predicted even in a case of separating and collecting unknown sample.

In the (E) analyzing step, the sample at the plurality of positions can be analyzed almost simultaneously. Also, the (B) inputting step and the (D) receiving step may be repeated for a plurality of times at a predetermined interval. In this case, a speed of travel of the sample along the channel is detected in the (E) analyzing step based on the plurality of positions and the predetermined interval.

According to the present invention, a method of detecting compositions in a microchip is provided. The microchip includes a clad layer having a channel, a plurality of light leading optical waveguides formed in the clad layer to intersect with the channel, and a light receiving optical waveguide formed along the channel in the clad layer. The method includes the steps of: (F) flowing a sample in the channel; (G) inputting a light to a plurality of positions of the channel sequentially by using the plurality of light leading optical waveguides; (H) the light passing through the sample at the plurality of positions; (I) receiving through respective of the plurality of light receiving optical waveguides sequentially the light passing through the plurality of positions; and (J) analyzing the sample flowing in the channel based on properties of the received light.

In the step (G) inputting the light sequentially, the light may be scanned at a speed substantially larger than a speed of the sample flowing through the channel. The scanning of the light is achieved by using a light from one light source. Also, the scanning can be achieved by providing a plurality of light sources which are connected to the ends of the plurality of light leading optical waveguides directly or through optical fibers and the like, and emitting the light sequentially from the plurality of light sources. Here, the speed of scanning the light can be set fast enough with regard to the speed of the sample along the channel to the extent that the positions of the sample are detectable. With this configuration, a similar detection result can be obtained as in the case when the lights are supplied to the plurality of light leading optical waveguides almost simultaneously. According to the method, it is possible to supply the light to the plurality of optical waveguides by using one light source.

The lights are introduced from the plurality of optical waveguides almost simultaneously, and the lights passing through the channel can be taken sequentially in relationship to the positions of the channel. Therefore, the separation pattern of the compositions of the sample can be detected. Conventionally, a microscope or a CCD is used for detecting a position of a sample flowing through a channel. However, in a case of detecting the position of the sample flowing through a fine channel, only an observation from above is possible by the microscope or the CCD, and only an image in a limited area can be obtained. Hence, images of the channel are taken from above for a plurality of times, and the separation pattern of the compositions of the sample is detected only by combining those images. Also, when a picture of a shallow channel is taken from above, it is not possible to obtain information regarding concentration of the compositions of the sample because of insufficient optical length. According to the method of detecting compositions of the present invention, the compositions in the channel can be detected based on the light passing through the channel along its width direction, merely by supplying sequentially the light emitted from the light source from the ends of the plurality of optical waveguides to the channel. Also, the information regarding the concentration of the sample compositions can be obtained on the basis of the intensity profile of the outputted light.

The (G) inputting step and the (I) receiving step may be repeated for a plurality of times at a predetermined interval. In this case, a speed of travel of the sample along the channel is detected in the (J) analyzing step based on the plurality of positions and the predetermined interval. Therefore, when the microchip of the present invention is used for separating the compositions of the sample, it is possible to detect a timing of collecting the compositions under the separating process. Particularly, in a case of separating and collecting unknown sample, it is possible to collect a target composition with certainty because the speed of travel of each composition can be detected, although it was not possible according to a conventional apparatus to detect the speed of travel of each composition of the sample. Also, since the speed of travel of the sample flowing through the channel is detected, it is possible to detect the compositions of the sample with higher accuracy based on the speed of travel.

According to the present invention, a method of detecting compositions in a microchip is provided. The microchip includes a clad layer having a channel and an optical waveguide formed in the clad layer to share a border with the channel. The method includes the steps of: (K) flowing a sample in the channel; (L) inputting a light from one end of the optical waveguide; (M) an interaction between an evanescent wave of the light and the sample occurring at a region where the optical waveguide is in contact with the channel; (N) receiving the light from another end the optical waveguide; and (O) analyzing the sample flowing in the channel based on properties of the received light.

According to the present invention, a method of detecting compositions in a microchip is provided. The microchip includes a clad layer having a channel, a light leading optical waveguide which is formed in the clad layer and branches into a first light leading optical waveguide and a second light leading optical waveguide intersecting with the channel, and a light receiving optical waveguide which is formed in the clad layer and branches into a first light receiving optical waveguide and a second light receiving optical waveguide intersecting with the channel. The method includes the steps of: (P) flowing a sample in the channel; (Q) dividing a light led from the light leading optical waveguide into a first light propagating in the first light leading optical waveguide and a second light propagating in the second light leading optical waveguide; (R) leading the first light to the channel through the first light leading optical waveguide; (S) leading the second light to the channel through the second light leading optical waveguide; (T) receiving the first light passing through the channel by the first light receiving optical waveguide; (U) receiving the second light passing through the channel by the second light receiving optical waveguide; (V) superposing the first light and the second light in the light receiving optical waveguide; and (W) analyzing the sample flowing in the channel based on properties of the superposed light.

According to the present invention, a method of detecting compositions in a microchip is provided. The microchip includes a clad layer having a channel, a light leading optical waveguide and a light receiving optical waveguide formed in the clad layer to intersect with the channel, and a heating optical waveguide having a border surface with respect to the channel, in which the heating optical waveguide is formed upstream of the light leading optical waveguide with respect to the channel and the border surface is colored. The method includes the steps of: (AA) flowing a sample in the channel; (BB) leading a heating light to the heating optical waveguide; (CC) heating the border surface between the heating optical waveguide and the channel by the heating light; (DD) heating the sample which is in contact with the heated border surface; (EE) a light led to the light leading optical waveguide passing through the heated sample; (FF) receiving the light through the light receiving optical waveguide; and (GG) analyzing the sample flowing in the channel based on properties of the received light.

According to the present invention, a method of detecting compositions in a microchip is provided. The microchip includes a clad layer having a channel, an optical waveguide formed in the clad layer along the channel, and a near-field prove whose tip reaches within the channel, in which the optical waveguide is exposed to the channel at a region facing the tip of the near-field probe. The method includes the steps of: (HH) flowing a sample in the channel; (II) leading a light to the near-field probe; (JJ) generating a near-field adjacent to the tip of the near-field probe; (KK) generating a scattered light by an interaction between the near-field and the sample; (LL) receiving the scattered light by the optical waveguide; and (MM) analyzing the sample flowing in the channel based on properties of the received scattered light.

According to the present invention, a method of detecting compositions in a microchip is provided. The microchip includes a clad layer having a channel, and a first optical waveguide and a second optical waveguide which are formed in the clad layer along the channel and have surfaces exposed to the channel. The method includes the steps of: (NN) flowing a sample in the channel; (OO) leading a light to the first optical waveguide; (PP) generating a near-field adjacent to the surface of the first optical waveguide exposed to the channel; (QQ) generating a scattered light by an interaction between the near-field and the sample; (RR) receiving the scattered light by the second optical waveguide; and (SS) analyzing the sample flowing in the channel based on properties of the received scattered light.

BRIEF DESCRIPTION OF DRAWINGS

FIG. 7 is a cross sectional view for showing a structure of a microchip according to a fourth embodiment of the present invention.

FIG. 9 is a schematic diagram for showing a modification of the microchip according to the fourth embodiment of the present invention.

BEST MODE FOR CARRYING OUT THE INVENTION

FIRST EMBODIMENT

Figure 1:
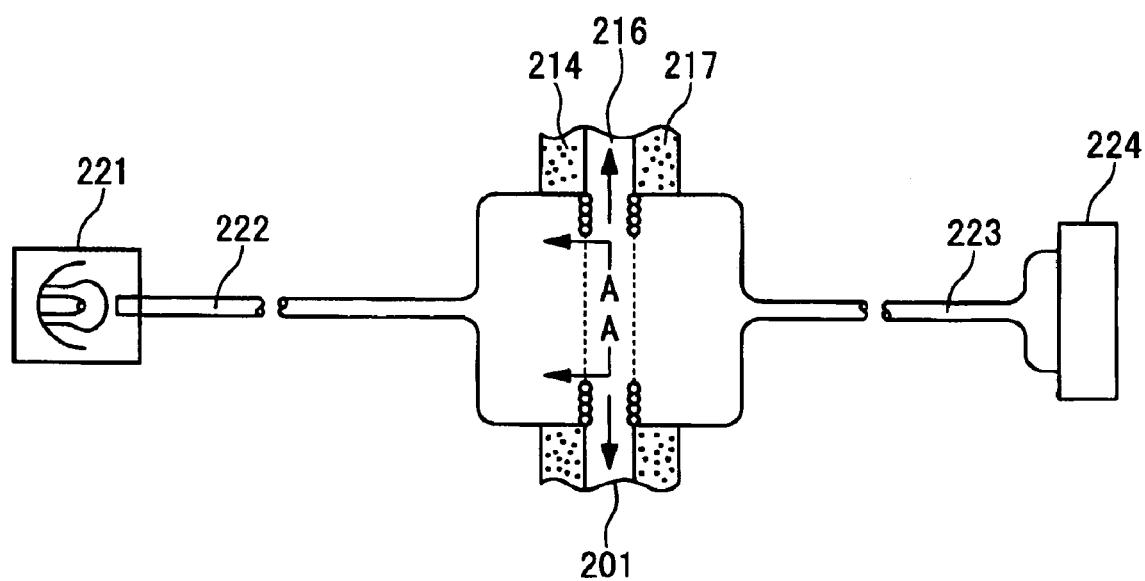
FIG. 1 is a diagram for showing a conventional densitometry apparatus.
Figure 2:
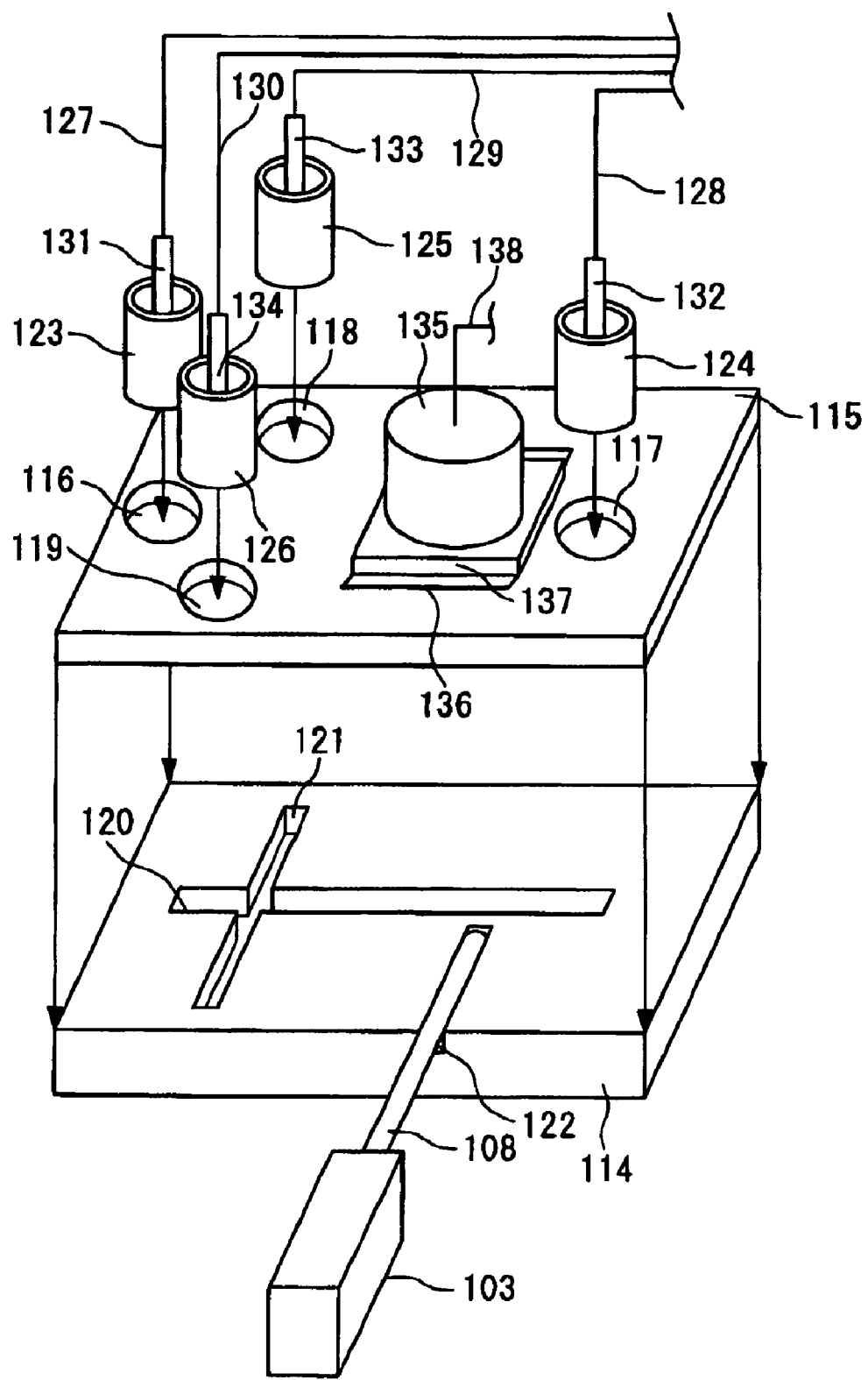
FIG. 2 is a diagram for showing a conventional capillary electrophoresis apparatus.
Figure 3A:
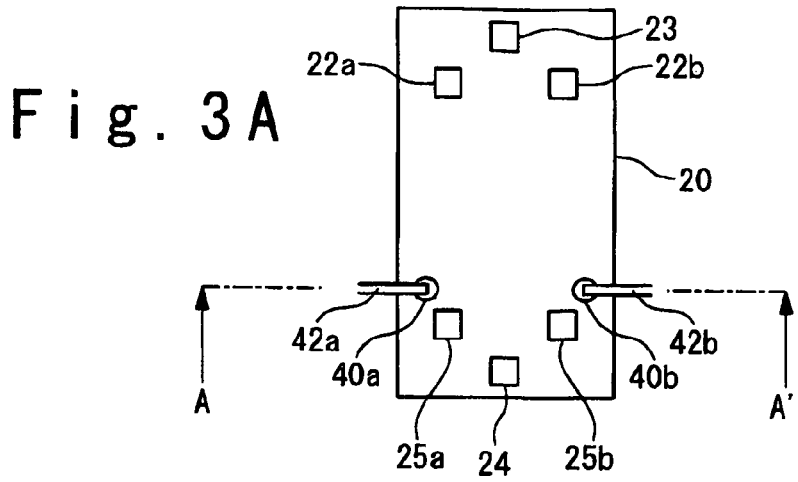
FIG. 3A is a schematic diagram for showing a microchip according to a first embodiment of the present invention.
Figure 3B:
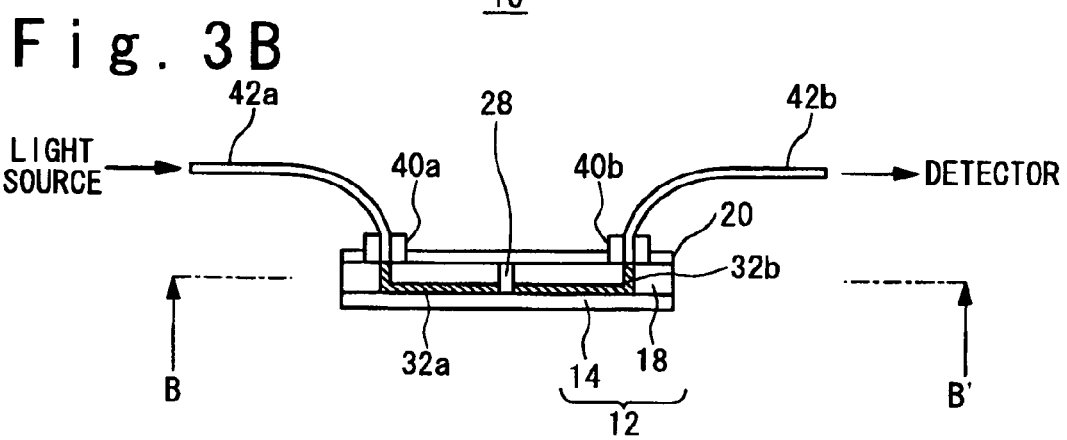
FIG. 3B is a cross sectional view along A–A' of the microchip in FIG. 3A.
Figure 3C:
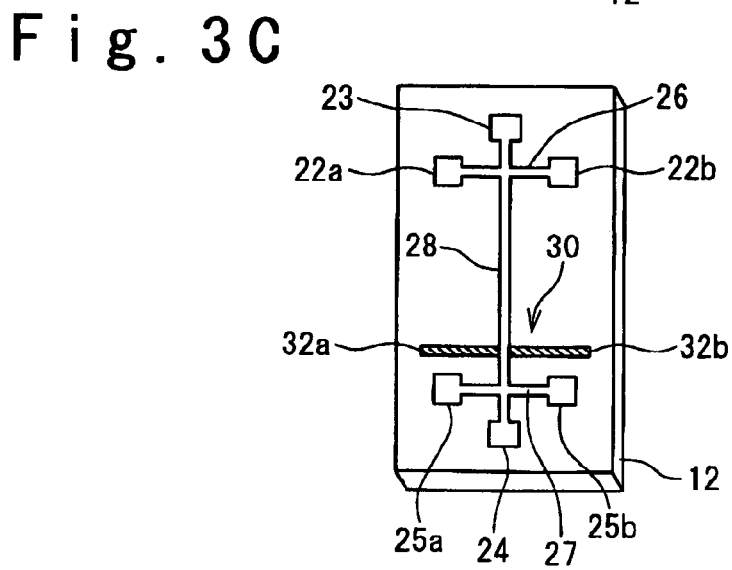
FIG. 3C is a cross sectional view along B–B' of the microchip in FIG. 3B.

FIGS. 3A to 3C are diagrams showing structures of a microchip according to a first embodiment of the present invention. The microchip 10 according to the present embodiment has a function capable of separating compositions contained in a sample. FIG. 3A is a top view of the microchip 10. The microchip 10 is provided with a liquid reservoir 22a, a liquid reservoir 22b, a liquid reservoir 23, a liquid reservoir 24, a liquid reservoir 25a, and a liquid reservoir 25b. Also, a light leading optical fiber 42a is connected via an optical connector 40a to the microchip 10, and a light receiving optical fiber 42b is connected via an optical connector 40b to the microchip 10.

FIG. 3B is a cross sectional view of the microchip along A–A' in FIG. 3A. The microchip 10 has a substrate 12 and a cover member 20. The substrate 12 includes a lower clad layer 14, and an upper clad layer 18 which is provided on the lower clad layer 14. A light leading optical waveguide 32a and a light receiving optical waveguide 32b are formed in the substrate 12. A separation channel 28 is provided between the light leading optical waveguide 32a and the light receiving optical waveguide 32b on a surface of the substrate 12. The light leading optical waveguide 32a and the light receiving optical waveguide 32b are used for detecting compositions contained in a sample which flows through the separation channel 28. The light leading optical fiber 42a is connected to an external light source (not shown), and the light receiving optical fiber 42b is connected to an external detector (not shown).

FIG. 3C is a cross sectional view of the microchip along B–B' in FIG. 3B. An input channel 26 is formed between the liquid reservoir 22a and the liquid reservoir 22b, a separation channel 28 is formed between the input channel 26 and the liquid reservoir 24, and a collection channel 27 is formed between the liquid reservoir 25a and the liquid reservoir 25b. A sensing section 30 is provided in the separation channel 28, and the light leading optical waveguide 32a and the light receiving optical waveguide 32b are arranged on both sides of the sensing section 30 to intersect with the separation channel 28. As a result, a sample which passes through the sensing section 30 can be optically detected and analyzed. Electrodes are provided for each of the liquid reservoirs 22a, 22b, 23, 24, 25a, and 25b, and a voltage can be applied to, for instance, both ends of the separation channel 28 by employing these electrodes.

Outer dimensions of the microchip 10 may be determined to proper values, depending upon the purpose thereof. In this embodiment, for example, a longitudinal dimension is from 5 mm to 5 cm, and a lateral dimension is from 3 mm to 3 cm. Also, a thickness of the lower clad layer 14 may be selected to be, for instance, 15 μm. A thickness of the cover member 20 may be selected to approximately 200 μm. A width of the separation channel 28 may be, for example, from 50 μm to 200 μm, which corresponds to a necessary optical length for detecting a transmission light in high precision when a light is led to the separation channel 28 from the light leading optical waveguide 32a, and then the light passing through the separation channel 28 is received from the light receiving optical waveguide 32b. A depth of the separation channel 28 may be, for instance, from 50 nm to 5 μm, which corresponds to a necessary depth with which compositions in the sample flowing in the separation channel 28 can be separated. Although no specific limitations are made as to thicknesses of the light leading optical waveguide 32a, the light receiving optical waveguide 32b and the upper clad layer 18, these thicknesses may be made thinner than the depth of the separation channel 28. Widths of the light leading optical waveguide 32a and the light receiving optical waveguide 32b may be, for example, from 1 μm to 5 μm.

The lower clad layer 14, the light leading optical waveguide 32a, the light receiving optical waveguide 32b, the upper clad layer 18 and the cover member 20 can be formed by employing either a quartz-series material or an organic-series polymer material. The light leading optical waveguide 32a and the light receiving optical waveguide 32b are formed to have higher refractive indexes than the lower clad layer 14 and the upper clad layer 18. The refractive indexes of these members are controlled in a proper manner according to a material, which will be described later.

Figure 17A:
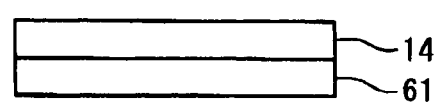
FIGS. 17A to 17H are diagrams for representing manufacturing steps as to the microchips shown in FIGS. 3A to 3C.
Figure 17E:
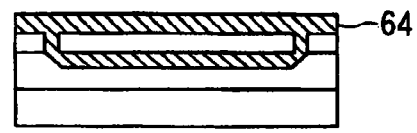
Figure 17B:
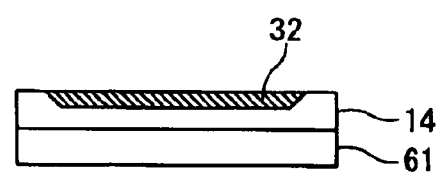

Referring now to FIGS. 17A to 17H and FIGS. 18A to 18D, a description is made of a method for manufacturing the microchip 10 in which the lower clad layer 14, the light leading optical waveguide 32a, the light receiving optical waveguide 32b, the upper clad layer 18 and the cover member 20 are made of the quartz series material. A base substrate 61 is made of either silicon or quartz glass. A lower clad layer 14 made of a quartz series film (BPSG: SiO2+ P2O5+B2O3) to which phosphorus (P) and boron (B) are added is formed on the base substrate 61 by employing an atmospheric pressure chemical vapor deposition method (APCVD by TEOS-03) in which an organic source made of tetraethylorthosilicate (Si(OC2H5)4) is decomposed by ozone (O3) (see FIG. 17A). Thereafter, a groove is formed in the lower clad layer 14, and an optical waveguide 32 is formed in the groove (FIG. 17B).

Figure 18A:
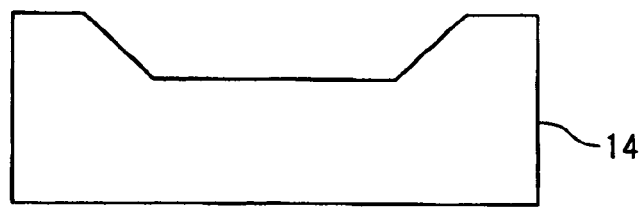
FIGS. 18A to 18D are diagrams for representing an example as to manufacturing steps of an optical waveguide of a microchip.
Figure 18B:
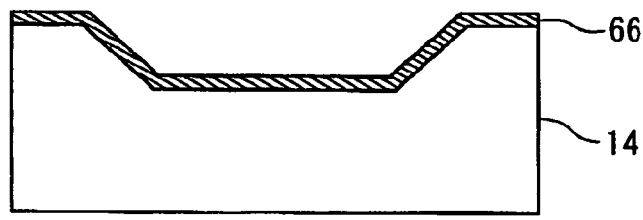
Figure 18C:
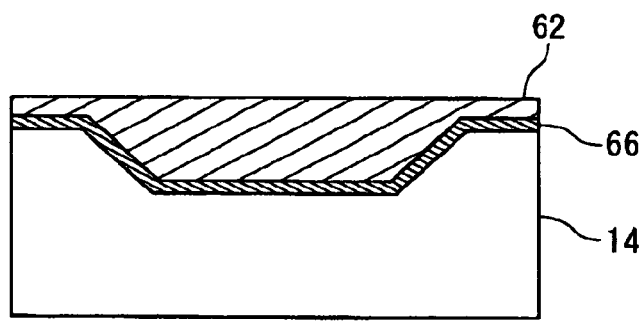
Figure 18D:
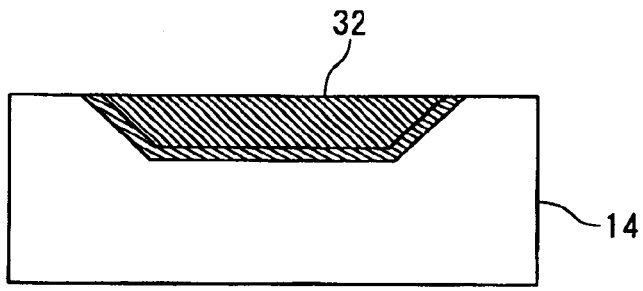

A manufacturing method of the optical waveguide 32 will be explained with reference to FIGS. 18A to 18D. First, the groove is formed in the lower clad layer 14 by way of both a photolithography and either a reactive ion etching (RIE) or a reactive ion beam etching (RIBE). A shape of this groove is formed in a desirable shape of the optical waveguide 32. In the present embodiment, an end section of the groove is formed to be a slope (FIG. 18A). Next, chromium or titanium or the like is vapor-deposited on a surface of the groove, on which gold, silver, or aluminum is vapor-deposited so as to form a reflective layer 66 (FIG. 18B). Next, a core layer 62 is formed on a whole surface of the lower clad layer 14 in such a manner that the core layer 62 is embedded in the groove (FIG. 18C). The core layer 62 is made of a quartz series film (GPSG: SiO2+P2O5+GeO2) to which phosphorus (P) and germanium (Ge) are added. Subsequently, both the reflective layer 66 and the core layer 62, which are formed outside the groove, are removed through a polishing so as to obtain an optical waveguide 32 having a predetermined shape (FIG. 18D). In this case, the optical waveguide 32 is formed to have a width of approximately 5 μm and a thickness of from 1 μm to 5 μm, for example. The optical waveguide 32 can be made further thinner, if the thickness thereof is made as such a dimension that a light having a wavelength conducted to the separation channel 28 can be transmitted.

Returning back to FIG. 17C, an upper clad layer 18 is formed on the lower clad layer 14 to cover the optical waveguide 32 (FIG. 17C). The upper clad layer 18 may be formed in a similar manner to that of the lower clad layer 14. After each of the films of the lower clad layer 14, the core layer 62 and the upper clad layer 18 is formed, it is preferable to perform an annealing treatment for each film. It should also be understood that various materials can be used in addition to the above-mentioned materials as the materials of the lower clad layer 14, the upper clad layer 18 and the core layer 62 (refer to FIG. 18C); such quartz series materials which contain either one or plural dopants selected from P, Ge, and B, or such as an SiON film, an SiN film and the like. The refractive indexes as to the lower clad layer 14, the core layer 62, and the upper clad layer 18 can be controlled by changing density of the dopant P, G, or B. Here, it is preferable that the refractive indexes of the lower clad layer 14 and the upper clad layer 18 are made equal to each other. In this case, a light leading optical waveguide 32a and a light receiving optical waveguide 32b, which will be formed later, can be surrounded by a material having the same refractive index. As a result, a transmission rate of the light in the light leading optical waveguide 32a and the light receiving optical waveguide 32b can be made higher.

Figure 17F:
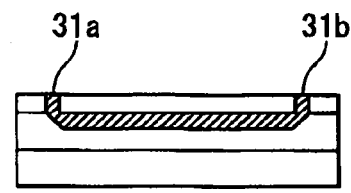
Figure 17C:
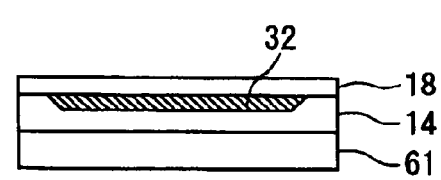
Figure 17G:
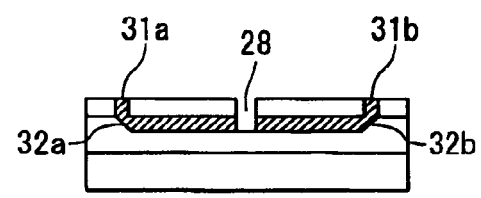
Figure 17D:
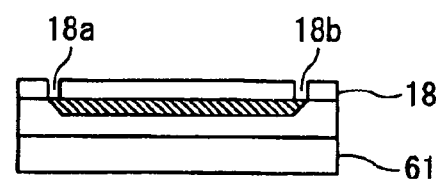

Next, connection holes 18a and 18b which reach to the optical waveguide 32 are formed in regions of the upper clad layer 18 over the optical waveguide 32 by way of an etching process (FIG. 17D). Then, a core layer 64 is deposited over the upper clad layer 18 in such a manner that these connection holes 18a and 18b are embedded. The core layer 64 is formed in a similar way by employing a similar material to that of the core layer 62 (FIG. 17E). Subsequently, the core layer 64 which is formed outside the connection holes 18a and 18b is removed by, for example, an RIE process. Thus, connection portions 31a and 31b are formed (FIG. 17F).

Figure 17H:
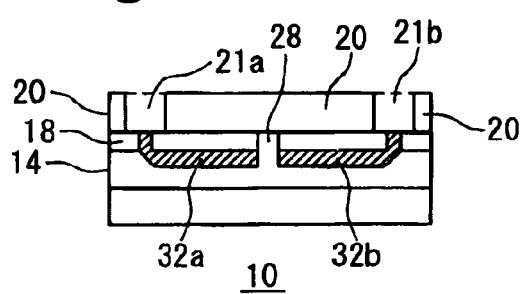

Next, a separation channel 28 which intersects with the optical waveguide 32 is formed by an etching process to divide the optical waveguide 32 into two sections. As a consequence, both a light leading optical waveguide 32a and a light receiving optical waveguide 32b are formed (FIG. 17G). It should also be noted that the surface of the separation channel 28 can be transformed to be a silicon oxide film by executing, for example, a thermal oxidation method and a chemical vapor deposition method (CVD). In this case, a water solution of a sample may flow through the separation channel 28. Next, a cover member 20 on which a connection portion 21a and a connection portion 21b are formed is provided on the upper clad layer 18, and then is fixed to the upper clad layer 18 by using adhesive agent and the like. Both the connection portion 21a and the connection portion 21b are formed such that these connection portions 21a and 21b are capable of accommodating therein optical connectors which hold optical fibers (FIG. 17H). In this case, sizes of these connection portions 21a and 21b may be formed in various sizes according to optical connectors to be connected thereto. For instance, a diameter of each of these connection portions may be made equal to 3 mm.

The microchip 10 can be manufactured in accordance with the above-described manufacturing method. Since the slopes where the reflective layers 66 are formed are provided on the end sections of the light leading optical waveguide 32a and the light receiving optical waveguide 32b, a light which is entered from an upper side can propagate via the light leading optical waveguide 32a and the light receiving optical waveguide 32b and can be outputted to the upper side again. By connecting the optical connectors holding the optical fibers to the microchip 10 manufactured as described above, a configuration as shown in FIGS. 3A to 3C can be obtained. The connections between the optical fibers and both the light leading optical waveguide 32a and the light receiving optical waveguide 32b of the microchip 10 may be carried out by employing various sorts of existing optical connectors. The optical fibers may be fixed to the microchip 10, or may be detachably connected to the microchip 10 by using detachable optical connectors.

Figure 4:
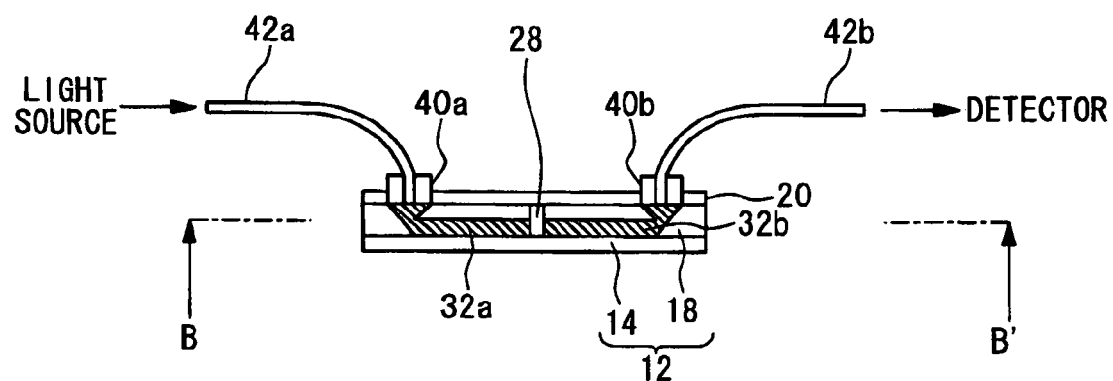
FIG. 4 is a schematic diagram for showing another example of a microchip according to the first embodiment of the present invention.

As indicated in FIG. 4, the light leading optical waveguide 32a and the light receiving optical waveguide 32b can be formed in such a manner that portions connecting to the light leading optical fiber 42a and the light receiving optical fiber 42b are wider than the other portions. In this case, the light leading optical waveguide 32a can be more firmly connected to the light leading optical fiber 42a, and also the light receiving optical waveguide 32b can be more firmly connected to the light receiving optical fiber 42b.

Next, a method for manufacturing the lower clad layer 14, the light leading optical waveguide 32a, the light receiving optical waveguide 32b, the upper clad layer 18, and the cover member 20 by using organic series polymer materials will now be explained. Also in this case, the manufacturing method is explained with reference also to FIG. 17A to FIG. 17H. First, after an epoxy resin is coated on the base substrate 61 by way of a spin coat method, a heating process operation is carried out so as to solidify the epoxy resin, to form the lower clad layer 14. Next, similar to the above-described example of the quartz glass with reference to FIG. 18A to FIG. 18D, a groove having a predetermined shape is formed in the lower clad larger 14 by way of a photolithography and either a reactive ion etching (RIE) process or a reactive ion beam etching (RIBE) process (FIG. 18A), and a reflective layer 66 is formed (FIG. 18B). Subsequently, similar to the method as to the lower clad layer 14, a core layer 62 is formed by employing such a material (for example, epoxy resin) having a higher refractive index than that of the material of the lower clad layer 14 (FIG. 18C). The reflective layer 66 and the core layer 62 which are formed outside the groove are removed, and hence an optical waveguide 32 having a predetermined shape is obtained (FIG. 18D). Next, similar to the method as to the lower clad layer 14, an upper clad layer 18 is formed on the entire surface of the base substrate 61 by using the same material as that of the lower clad layer 14 (FIG. 17C). It should also be noted that the lower clad layer 14, the core layer 62, and the upper clad layer 18 may be alternatively formed in such a manner that after a photo-curing resin is coated on a corresponding base layer, a light is irradiated to the photo-curing resin so as to cure the resin.

Thereafter, connection holes 18a and 18b are formed by way of, for example, an RIE process (FIG. 17D). Then, similar to the method as to the core layer 62, a core layer 64 is formed by employing the same material as that of the core layer 62 (FIG. 17E). Subsequently, the core layer 64 which is formed outside the connection holes 18a and 18b is removed by way of, for example, an RIE process, so as to form connection portions 31a and 31b (FIG. 17F). Next, a photoresist film is formed on the upper clad layer 18, and then a predetermined exposing process and a predetermined developing process are carried out with respect to the photoresist film. Hence, the photoresist film is processed to have a predetermined pattern corresponding to the separation channel 28. Next, an anisotropic etching of the optical waveguide 32 is carried out by way of, for example, an RIE process by using the photoresist film as a mask. As a result, the separation channel 28 which intersects with the optical waveguide 32 is formed. Thereafter, the photoresist film is removed (FIG. 17G).

As previously explained, according to the present embodiment, after the optical waveguide 32 is formed on the lower clad layer 14, the separation channel 28 is formed so as to divide the optical waveguide 32 into both the light leading optical waveguide 32a and the light receiving optical waveguide 32b. As a consequence, the conventional problem as to positioning between the light leading optical fiber and the light receiving optical fiber can be solved.

Figure 19A:
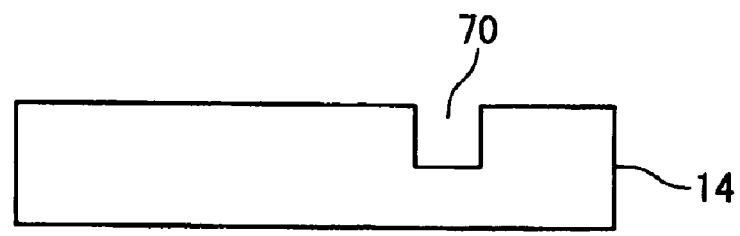
FIGS. 19A to 19C are diagrams for representing an example as to manufacturing steps of a microchip.
Figure 19B:
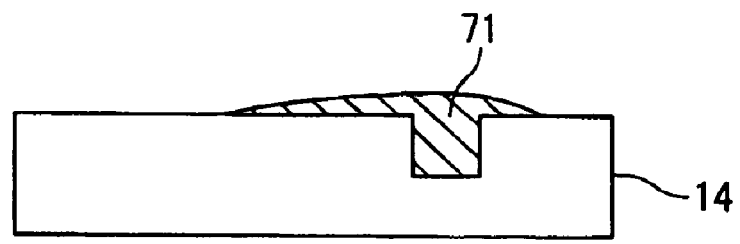
Figure 19C:
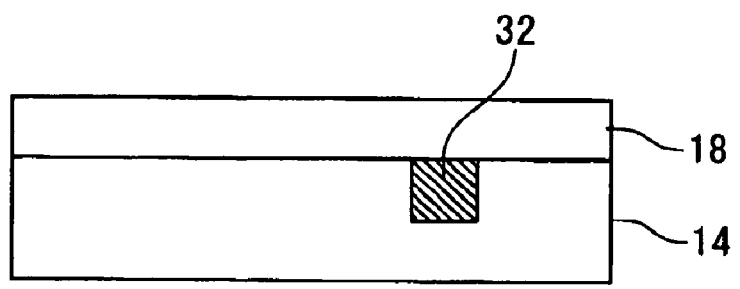
Figure 20A:
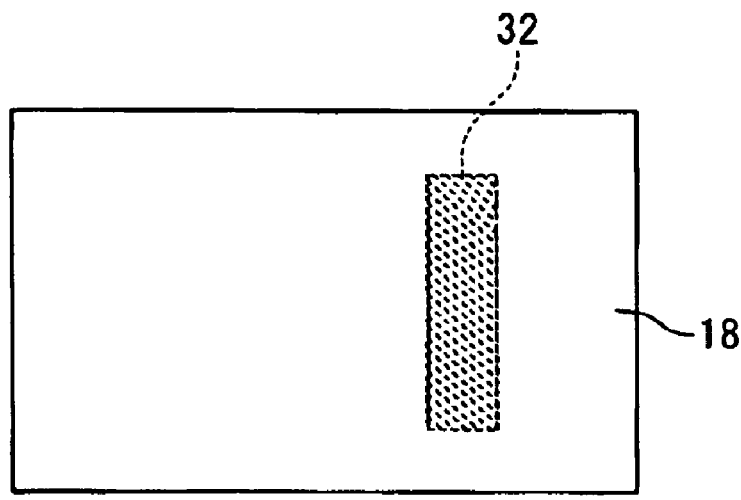
FIGS. 20A and 20B are diagrams for representing an example as to manufacturing steps of a microchip.
Figure 20B:
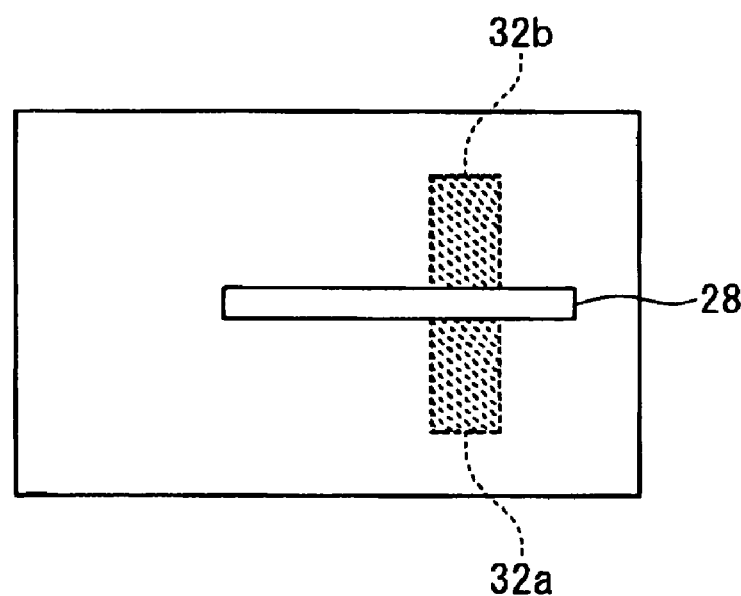

Also, the light leading optical waveguide 32a and the light receiving optical waveguide 32b may be manufactured in accordance with the below-mentioned method. Referring now to FIGS. 19A to 19C, and FIGS. 20A and 20B, the manufacturing method will be explained. First, a master is formed by executing either a machining process or an etching process, and then, a lower clad layer 14 is formed in which a groove 70 is formed by performing either an injection molding method or an injection compression molding method by the use of a die which is manufactured by electric-casting-inverting the master. Also, in this case, an end section of the groove 70 is formed to have a slope shape, and a surface of the shape is processed by a mirror surface treatment (FIG. 19A). Thereafter, a core layer material 71 in a monomer condition is coated on the groove 70 of the lower clad layer 14 (FIG. 19B). A refractive index of the core layer material 71 becomes higher than that of the lower clad layer 14 when being cured. The upper clad layer 18 which is made of a similar material to that of the lower clad layer 14 is depressed from the above by employing a clamping jig. After the extra core layer materials 71 are removed, ultra-violet rays are irradiated to the entire portion so as to cure the core layer material 71 (FIG. 19C). FIG. 20A is an top view of a substrate which is manufactured in this manner. On the substrate manufactured in this manner, a separation channel 28 can be formed by performing, for instance, an RIE method such that both the light leading optical waveguide 32a and the light receiving optical waveguide 32b are formed (FIG. 20B).

Figure 21A:
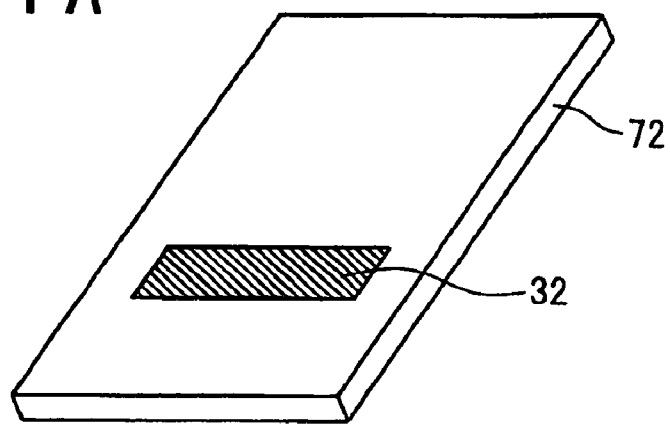
FIGS. 21A to 21C are diagrams for representing an example as to manufacturing steps of a microchip.
Figure 21B:
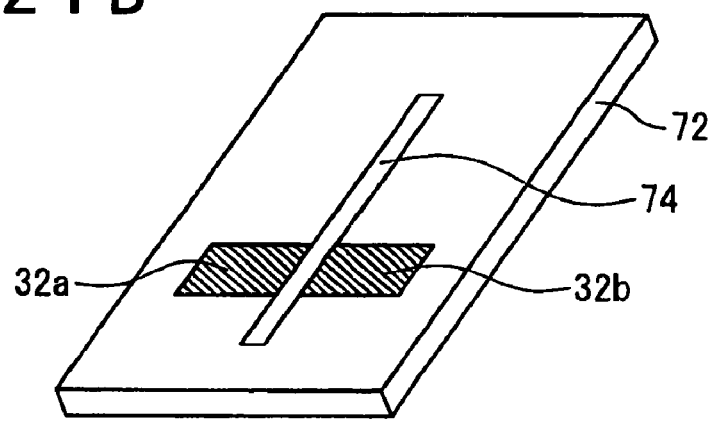
Figure 21C:
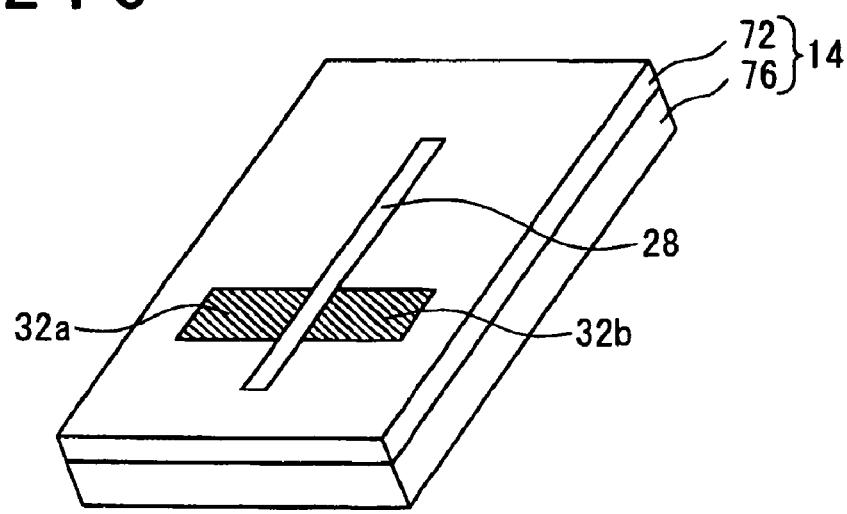

Also, as represented in FIG. 21A, a film-shaped clad seat 72 may be prepared in which an optical waveguide 32 is formed on a predetermined area. Then, an opening portion 74 is formed by punching an area corresponding to the separation channel 28 by a die (FIG. 21B). After that, the lower clad layer 14, the separation channel 28, the light leading optical waveguide 32a, and the light receiving optical waveguide 32b can be manufactured by bonding the clad seat 72 to a clad substrate 76 which is made of the same material as the material of the clad seat 72 (FIG. 21C). In this case, the bonding of the clad seat 72 and the clad substrate 76 can be performed by an ultrasonic crimping process, a thermal crimping process or by using adhesive agent.

The lower clad layer 14, the light leading optical waveguide 32a, the light receiving optical waveguide 32b, the upper clad layer 18, and the cover member 20 can be made of various sorts of materials depending upon the purpose. Here, the light leading optical waveguide 32a and the light receiving optical waveguide 32b may be made of such a material whose refractive index is higher than that of the material for constituting both the lower clad layer 14 and the upper clad layer 18. For instance, both the lower clad layer 14 and the upper clad layer 18 may be made of an epoxy resin whose refractive index is about 1.52, whereas both the light leading optical waveguide 32a and the light receiving optical waveguide 32b may be made of an epoxy resin whose refractive index is about 1.54. If such a condition is satisfied that the refractive indexes of both the light leading optical waveguide 32a and the light receiving optical waveguide 32b are larger than the refractive indexes of both the lower clad layer 14 and the upper clad layer 18, then the lower clad layer 14, the light leading optical waveguide 32a, the light receiving optical waveguide 32b, the upper clad layer 18, and the cover member 20 can be made of other materials: for instance, acrylic resins such as polyimide and polymethyl methacrylate (PMMA); polyolefin resins such as polyethylene, polystyrene, and tube polyolefin; PDMS; or synthetic rubber.

In a case when the lower clad layer 14 and the optical waveguide 32 are made of a material having a hydrophobic property, after the separation channel 28 is formed, a surface processing operation may be carried out in order to apply a hydrophilic property. As the surface processing operation in order to apply the hydrophilic property, for instance, a coupling agent having a hydrophilic group may be coated onto the side wall of the separation channel 28. As the coupling agent having the hydrophilic group, for example, a silane coupling agent having an amino group may be considered. More specifically, N-β(aminoethyl)γ-aminopropyl-methyldimethoxysilane, N-β(aminoethyl)γ-aminopropyltri-methoxysilane, N-β(aminoethyl)γ-aminopropyltriethoxysilane, γ-aminopropyltrimethoxysilane, γ-aminopropyltriethoxysilane, N-phenyl-γ-aminopropyltriethoxysilane and so on are exemplified. These coupling agents may be coated by performing a spin coat method, a spray method, a dip method, a vapor deposition method and the like. Also, in order to avoid that molecules of a sample are adhered to a channel wall, an adhesion preventing process may be carried out with respect to the separation channel 28. As the adhesion preventing process, for example, such a substance having a structure similar to phosphorous lipid for constituting a cell wall may be coated on the side wall of the separation channel 28. In a case when a sample corresponds to biological composition such as protein and the like, it is possible with this process to prevent the denaturation of the composition. Moreover, it is possible to suppress nonspecific adhesion of a specific composition in the separation channel 28, and hence to improve the recovery. With regard to the hydrophilic process and the adhesion preventing process, for example, "Lipidure" (registered trademark owned by Nihon Yushi K.K) may be employed. In this case, the "Lipidure" (registered trademark) is solved into a buffer solution such as TBE buffer such that the "Lipidure" becomes 0.5 wt %. Then, the separation channel 28 is filled with the liquid solution and is left for several minutes, so that the inner wall of the separation channel 28 can be processed. After that, the liquid solution is blown away by using an air gun and the like, and the separation channel 28 is dried. As another example of the adhesion preventing process, for example, fluorocarbon polymers may be coated onto the side wall of the separation channel 28.

Returning back to FIGS. 3A to 3C, a description is made of a method for separating and detecting compositions contained in a sample by using the microchip 10. Prior to the detection of the compositions of the sample, the light leading optical waveguide 32a of the microchip 10 is connected via the light leading optical fiber 42a to an external light source, and the light receiving optical waveguide 32b is connected via the light receiving optical fiber 42b to an external detector. Various kinds of apparatuses such as an absortiometer and the like can be used as the detector, which are capable of detecting properties of light which is transmitted via the light receiving optical fiber 42b.

First, a sample is injected into either the liquid reservoir 22a or the liquid reservoir 22b. In the case that the sample is injected into the liquid reservoir 22a, a voltage is applied such that the sample flows to the liquid reservoir 22b. In the case that the sample is injected into the liquid reservoir 22b, a voltage is applied such that the sample flows to the liquid reservoir 22a. As a result, the sample flows into the injection channel 26, and the entire portion of the injection channel 26 is filled with the sample. At this time, the sample is present only at a cross point with respect to the injection channel 26 on the separation channel 28.

Next, the application of the voltage between the liquid reservoir 22a and the liquid reservoir 22b is stopped, and a voltage is applied between the liquid reservoir 23 and the liquid reservoir 24 in such a manner that the sample flows to the liquid reservoir 24. As a result, the sample flows through the separation channel 28. The microchip 10 can separate the compositions contained in the sample in the separation channel 28 by utilizing, for example, a principle of the capillary electrophoresis. As a consequence, the sample which passes through the separation channel 28 is separated into various bands of composition. Alternatively, the separation channel 28 may be configured to have a large number of pillar-shaped structures therein which are formed by, for example, a nano-meter processing technique and are arranged with a constant interval. A degree at which the sample easily passes through the intervals of the pillar-shaped structures arranged in the above-described manner changes according to the sizes of molecules. Thus, when the sample containing the molecules with various sizes is conducted into the separation channel 28 where a large number of pillar-shaped structures are arranged, speeds at which the molecules flow through the separation channel 28 are different from each other in accordance with the dimensions thereof, and hence the molecules are separated into bands moving at the different speeds. Here, a band indicates a group having a narrow width which is formed by each of the compositions contained in the sample.

When these separated bands arrive at the sensing section 30, the separated bands are detected by an optical method. In the optical detecting method, for instance, a visible light/ultraviolet absorption spectrum (UV spectrum) method may be employed. For example, protein exhibits a ultraviolet absorption spectrum having a local maximum near 280 nm, whereas both DNA and RNA exhibit maximal values in the vicinity of 260 nm. As a consequence, in a case when protein, DNA, or RNA is set to a target for detection, the light leading optical waveguide 32a and the light receiving optical waveguide 32b are preferably made of a material having a UV transmission characteristic. Also, in a case of chromoprotein such as hemoglobin and so on, the chromoprotein exhibits an absorption spectrum having a local maximum in the vicinity of 550 nm. Both the light leading optical waveguide 32a and the light receiving optical waveguide 32b can be made of such a material which transmits therethrough a light with a wavelength corresponding to a local maximum of an absorption spectrum of a target composition. A light emitted from the external light source is supplied to the sensing section 30 through the light leading optical waveguide 32a. Then, the light which passes through the separated bands within the separation channel 28 is transmitted via the light receiving optical waveguide 32b to an external detector. Accordingly, the external detector can detect properties such as an intensity of the light passing through the separated bands. If the target is a known substance, it is possible to detect concentration of the sample on the basis of absorbance of the sample by using an absorbance index of the substance. The separated bands may be further collected every band. When a desired band passes through the sensing section 30, the application of the voltage between the liquid reservoir 23 and the liquid reservoir 24 is stopped. Instead, a voltage is applied between the liquid reservoir 25a and the liquid reservoir 25b. As a result, the band located at a cross point of the separation channel 28 and a collection channel 27 flows into the collection channel 27. When the application of the voltage between the liquid reservoir 25a and the liquid reservoir 25b is stopped after a predetermined time period is elapsed, the desired composition contained in the separated band is collected to either the liquid reservoir 25a or the liquid reservoir 25b. In the microchip 10 according to the present embodiment, a technique is employed in which the sample is caused to be moved by applying the voltage. The application of voltage can be substituted by a technique in which a pressure is applied or a technique in which the sample is caused to be moved due to the capillary phenomenon.

The microchip 10 according to the present embodiment can be applied for detecting and quantifying various sorts of substances. Applications of this microchip 10 is exemplified in blood biological investigations, immune serum investigations, and analyses of tumor markers. The blood biological investigations investigate glucose, alanineaminotransferase, albumin, alkaline phosphatase, amylase, calcium ion, total cholesterol, lipid peroxide, creatine, potassium ion, bilirubin, total protein etc. The immune serum investigations investigate Hbs antigen/antibody, HCV antibody, HIV antibody etc. The tumor markers contain CEA, CA19-9, PSA, CA-125 etc.

In the case that glucose is detected, either mixed fine particles having coloring characteristics such as glucose oxidase, peroxidase, and 4-aminoantipyrine and N-ethyl-N-(2-hydroxy-3-sulfopropyl)-m-toluidine sodium or dried reagent beads containing these mixed fine particles are conducted into the sensing section 30 of the separation channel 28. In this case, presence of glucose can be confirmed based upon the coloring phenomenon of the mixed fine particles having the coloring characteristics. The principle is given as follows. When glucose is transferred into the above-explained reagent which has absorbed water compositions to become gel reagent beads, the glucose is decomposed to hydrogen peroxide and gluconic acid due to an effect of glucose oxidase. The generated hydrogen peroxide reacts with 4-aminoantipyrine and N-ethyl-N-(2-hydroxy-3-sulfopropyl)-m-toluidine sodium due to an effect of peroxidase. As a result, xenon-series dye is generated, and is colored in red purple. By measuring the color of the xenon-series dye, glucose can be quantified. Since the microchip 10 according to the present embodiment can be formed to have a very fine structure, a measurement in high precision is possible even in a case of very small amounts of a sample.

It should also be noted that the above-described dried reagent beads can be manufactured as follows: That is, first of all, as an excipient, sol is arranged which contains water absorptive polymers such as agarose, polyacrylamide, and methylecellulose and so on. The sol formed in this manner is naturally brought into gel while time has elapsed. This sol is mixed with a predetermined amount of glucose oxidase, peroxidase, 4-aminoantipyrine and N-ethyl-N-(2-hydroxy-3-sulfopropyl)-m-toluidine sodium. The resulting sol is sprayed in dried air so as to become liquid droplets. Since the liquid droplets are brought into gel and is dried while being dropped, the desired dried reagent beads can be obtained.

Alternatively, the below-mentioned method may be employed as the method for manufacturing the above-described dried reagent beads. That is, sol containing the above-described reagent is made to gel on a surface of a flask and the like, and then is freeze-dried. As a result, a solid material having a large number of vacuoles can be obtained. This solid material can be easily broken into either beads or powder.

Next, a description is made of a method for filling the dried reagent beads which are formed in the above-described manner into the microchip 10. First, a proper amount of water absorbing member is previously inserted from the liquid reservoir 23. Next, a mixed article made of the above-explained dried reagent beads and water is supplied from the liquid reservoir 23. This dried reagent beads are moved within the separation channel 28 to the liquid reservoir 24 due to the capillary phenomenon, so that the dried reagent beads are filled into the microchip 10. Water compositions contained in the dried reagent beads are absorbed by the above-explained water absorbing member. After the water compositions are absorbed by the water absorbing member, the water absorbing member is removed. Then, the microchip 10 is dried by way of vacuum drying, drying under reduced pressure, or freeze-dry lyophilization. Thus, the dried reagent beads can be filled into the separation channel 28 of the microchip 10. Alternatively, for instance, both reagent and a binder may be solved into a solution, or may be uniformly suspended; either this solution or the suspension may be entered into the separation channel 28; the entered solution, or the entered suspension may be dried by way of vacuum drying, drying under reduced pressure, or freeze-dry lyophilization. As a result, the mixed fine particles having the coloring characteristics can be filled into the microchip 10.

Also, for the purpose of detecting an HCV antibody contained in the sample, for instance, a solid layer immune quantifying method and an ELISA (Enzyme-Lincked immuno-sorbent Assay) method can be employed. In this case, core protein corresponding to the structural protein of HCV is adhered to the bottom surface of the sensing section 30 of the separation channel 28. More specifically, since a buffer to which this core protein is dispersed is conducted into the separation channel 28, this core protein may be adhered to the bottom surface of the separation channel 28. Thereafter, when an HCV antibody which recognizes the core protein is contained in the sample, the antibody is coupled with the core protein to form an antibody-antigen composite body. Next, buffer is supplied from the liquid reservoir 22a or the liquid reservoir 22b, and then the buffer is penetrated through the separation channel 28 so as to clean the inside of the separation channel 28. Then, a polyclonal antibody (secondary antibody) which recognizes the HCV antibody is conducted to the separation channel 28, and the secondary antibody is further coupled with the antibody-antigen composite body so as to again clean the inside of the separation channel 28 in a similar manner. At this time, by coupling the secondary antibody with either a fluorescent mark or enzyme such as alkali phosphatase, it is possible to achieve the detection of the HCV antibody with a high sensitivity. In the case when the fluorescent mark is coupled with the secondary antibody, it is possible to confirm the presence of the HCV antibody by irradiating the inside of the separation channel 28 by using a black light and so on. On the other hand, in the case when the alkali phosphatase is coupled with the secondary antibody, if a coloring substrate such as p-nitophenylphosphate is supplied to the separation channel 28, then enzyme reaction occurs due to alkali phosphatase, and thus, the coloring substrate emits a color. As a result, the HCV antibody can be detected.

In the above description, the HCV antibody is exemplified when the antibody contained in the sample is detected. Alternatively, for the purpose of detecting specific protein contained in a sample, for instance, core protein corresponding to the structural protein of HCV, the below-mentioned method may be employed. A monoclonal antibody (primary antibody) which recognizes an area of a terminal "N" of core protein corresponding to the structure protein of HCV is previously coupled to the bottom surface of the separation channel 28. A sample is supplied from either the liquid reservoir 22a or the liquid reservoir 22b, and then, is moved to the separation channel 28 due to the capillary phenomenon. When the above-mentioned core protein is contained in the sample, the primary antibody is coupled to the core protein, so that an antibody-antigen composite body is formed. Next, a similar process operation to the above case is carried out so as to clean the inside of the separation channel 28. Then, a monoclonal antibody (secondary antibody) which recognizes an area other than the terminal "N" of the core protein is supplied to the separation channel 28, and the secondary antibody is further coupled to the antibody-antigen composite body so as to again clean the inside of the separation channel 28 in a similar manner to the above manner. At this time, since either a fluorescent mark or enzyme such as alkaline phosphatase is coupled to the secondary antibody, an HCV antigen can also be detected in a high sensitivity in accordance with a similar manner to the above-described case of the HCV antibody.

SECOND EMBODIMENT

Figure 5:
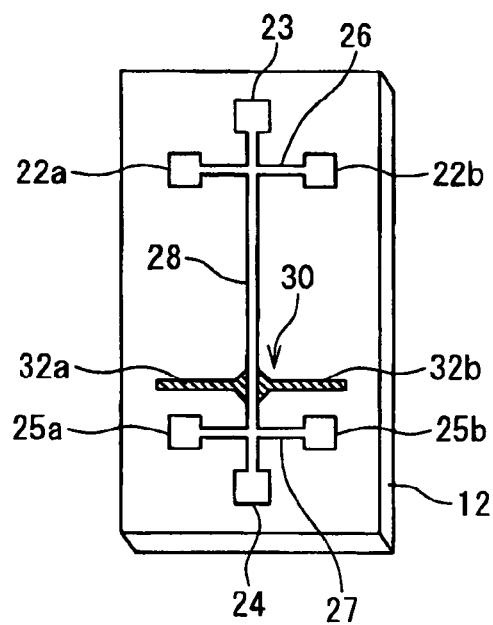
FIG. 5 is a cross sectional view for showing a structure of a microchip according to a second embodiment of the present invention.

FIG. 5 is a cross sectional view showing a structure of a microchip according to a second embodiment of the present invention. In the present embodiment, the same reference numerals in the first embodiment shown in FIG. 3C are given to the same components, and explanations thereof are properly omitted.

When a light which is transmitted from the external light source via the light leading optical waveguide 32a is entered to the separation channel 28, the entered light is broadened and scattered within the separation channel 28. In this case, an amount of light which is transmitted to the light receiving optical waveguide 32b is decreased. Therefore, according to the present embodiment, the light leading optical waveguide 32a and the light receiving optical waveguide 32b are formed in such a manner that these optical waveguides 32a and 32b have wide width portions at boundaries with respect to the separation channel 28. The wide width portions are made wider than the other regions. For example, the widths of the other regions of both the light leading optical waveguide 32a and the light receiving optical waveguide 32b may be set to approximately 5 µm, whereas the widths at the boundaries with respect to the separation channel 28 may be set to approximately 10 µm. As a consequence, the decrease of the amount of the light which is transmitted to the light receiving optical waveguide 32b can be suppressed, and a sufficient amount of the light can be transmitted to the external detector. It is thus possible to detect the compositions contained in the sample in higher precision.

Also, as indicated in FIG. 4, both the light leading optical waveguide 32a and the light receiving optical waveguide 32b can be made wider at portions which are connected to the light leading optical fiber 42a and the light receiving optical fiber 42b, respectively.

THIRD EMBODIMENT

Figure 6A:
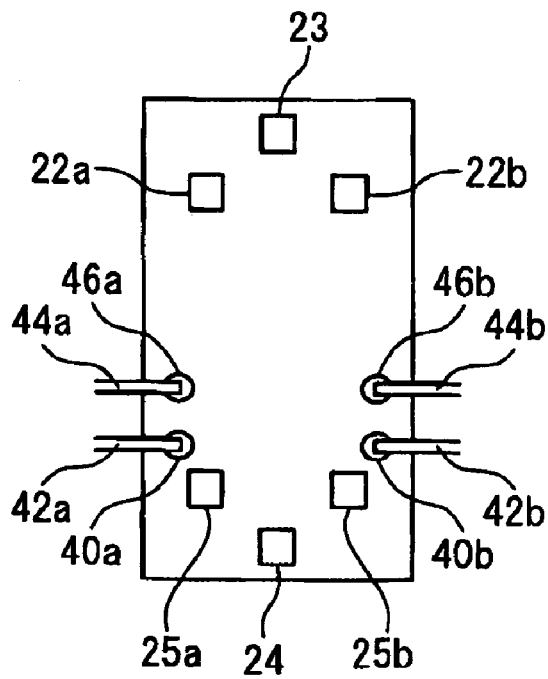
FIG. 6A is a schematic diagram for showing a microchip according to a third embodiment of the present invention.
Figure 6B:
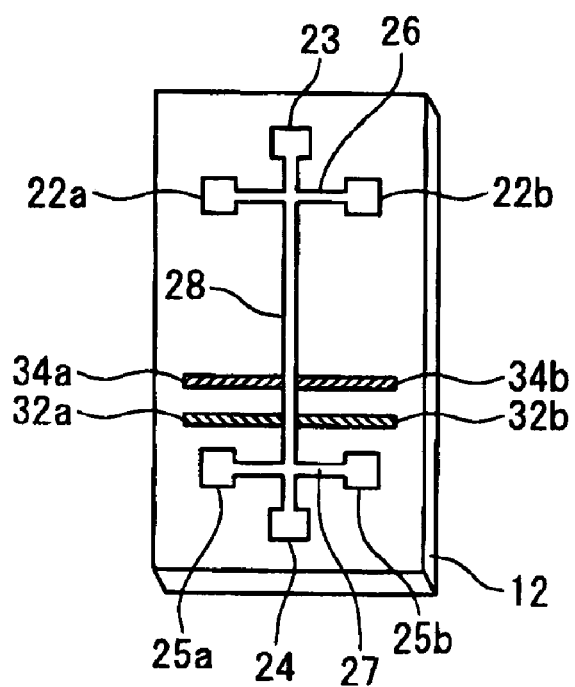
FIG. 6B is a cross sectional view for showing a structure of the microchip according to the third embodiment of the present invention.

FIG. 6A is a schematic diagram for showing a microchip according to a third embodiment of the present invention. FIG. 6B is a cross sectional view showing the microchip in FIG. 6A. In the present embodiment, the same reference numerals in the first embodiment shown in FIGS. 3A and 3C are given to the same components, and explanations thereof are properly omitted.

According to the present embodiment, a microchip 52 is different from the first embodiment in that the microchip 52 has not only a combination of a light leading optical waveguide 32a and a light receiving optical waveguide 32b but also a combination of a light leading optical waveguide 34a and a light receiving optical waveguide 34b. The light leading optical waveguide 32a and the light receiving optical waveguide 32b are provided opposite to each other on both sides of the separation channel 28. Also, the light leading optical waveguide 34a and the light receiving optical waveguide 34b are provided opposite to each other on both sides of the separation channel 28.

According to the configuration in the present embodiment, it is possible to analyze simultaneously the samples which flow at different positions in the separation channel 28. For example, any one of the combination of the light leading optical waveguide 32a and the light receiving optical waveguide 32b and the combination of the light leading optical waveguide 34a and the light receiving optical waveguide 34b can be used as a reference. In this case, measured data can be corrected by using reference data which are measured under the same condition. It is thus possible to analyze the sample in higher precision.

Also, since the samples at the different positions in the separation channel 28 are analyzed, speed of travel of each of the separated samples can be detected. As a consequence, it is possible to detect a timing of collecting the compositions of the sample under separation process. In particular, even in a case when an unknown sample is separated and collected, a flow-out time of each composition can be predicted. It is therefore possible to collect a target composition firmly.

Also in the present embodiment, the light leading optical waveguide 32a and the light receiving optical waveguide 32b, and the light leading optical waveguide 34a and the light receiving optical waveguide 34b can be made wider at the portions connecting to the outside of the microchip, as shown in FIG. 4. Also, they can be made wider at the boundaries with respect to the separation channel 28 than the other regions, as shown in FIG. 5.

FOURTH EMBODIMENT

FIG. 7 is a cross sectional view showing a structure of a microchip according to a fourth embodiment of the present invention. In the present embodiment, the same reference numerals in the first embodiment shown in FIG. 3C are given to the same components, and explanations thereof are properly omitted. The microchip 54 is different from the first embodiment in that the microchip 54 has a plurality of light leading optical waveguides 56 and also has a light receiving optical waveguide 58 which is provided opposite to the plurality of light leading optical waveguides 56 across the separation channel 28.

In the present embodiment, the plurality of light leading optical waveguides 56 are formed substantially perpendicular to a direction in which the sample flows through the separation channel 28. The plurality of light leading optical waveguides 56 are formed apart from each other with a predetermined interval. Also, the light receiving optical waveguide 58 is formed along the separation channel 28 substantially parallel to the direction in which the sample flows through the separation channel 28. In the present embodiment, a width of one light leading optical waveguide 56 is formed wider than or equal to 3 µm, and the plurality of light leading optical waveguides 56 are arranged apart from each other with an interval longer than or equal to 6 µm. A width of the light receiving optical waveguide 58 is made wider than or equal to 3 µm.

Each of the light leading optical waveguides 56 is formed in such a manner that the light emitted from the external light source can enter thereinto at a position different from one end 56a which is in contact with the separation channel 28. For instance, in the present embodiment, each of the light leading optical waveguides 56 is formed in such a manner that the light emitted from the external light source can enter thereinto from the other end 56b which is located opposite to the one end 56a which is in contact with the separation channel 28. The light emitted from the external light source is directly supplied, or indirectly supplied via an optical fiber and the like from the other end 56b of the light leading optical waveguide 56. In this case, by scanning one external light source, it is possible to lead the light sequentially to respective of the other ends 56b of the plurality of light leading optical waveguides 56. Also, light emitting diodes (LEDs) can be directly connected, or indirectly connected via optical fibers to respective of the other ends 56b of the plurality of light leading optical waveguides 56.

In this case, by emitting a light sequentially from the light emitting diodes, it is possible to lead the light sequentially to respective of the other ends 56*b* of the plurality of light leading optical waveguides 56. In the present embodiment, the light is sequentially entered to the plurality of light leading optical waveguides 56 by focusing the light emitted from one external light source by using a focusing lens 60, and scanning the one external light source.

The light receiving optical waveguide 58 is configured to be connectable with the external detector. For instance, according to the present embodiment, an end section 58*a* of the light receiving optical waveguide 58 is formed to be a slope and is treated to be a mirror plane. As a result, the light which is transmitted through the light receiving optical waveguide 58 can be transmitted to the upper at the end section 58*a*. As in the case of microchip 10 shown in the first embodiment, the light can be emitted to the upper of the microchip 54. Such a structure can be formed in a similar manner to the manner which is explained in the first embodiment with reference to FIGS. 17A to 17H and FIGS. 18A to 18D.

Next, a description is made of a method of separating the samples by using the microchip 54, and measuring intensity of a light which is irradiated to the separated samples and penetrates through the samples. In this case, the light receiving optical waveguide 58 of the microchip 10 is connected to an external detector (not shown).

As is explained in the first embodiment, a sample is first injected into both the liquid reservoir 22*a* and the liquid reservoir 22*b*. The sample passes through the respective injection channels 26, and then is conducted to the separation channel 28 at such a position that the injection channel 26 intersects with the separation channel 28. In this case, the sample in the separation channel 28 is moved to the liquid reservoir 24 due to the application of a voltage.

Subsequently, as represented in the drawing, the light emitted from the external light source is focused by the focusing lens 60, and the light is scanned such that the light is sequentially supplied to the other ends 56*b* of the respective of the light leading optical waveguides 56. The light which is supplied from the other end 56*b* of each of the light leading optical waveguides 56 propagates in each light leading optical waveguide 56, and then led to the separation channel 28 through the corresponding one end 56*a*. The light which passes through the sample flowing in the separation channel 28 propagates through the light receiving optical waveguide 58 and is transmitted to the external detector from the end section 58*a* of the light receiving optical waveguide 58. As a result, intensity of the light which passes through the sample flowing in the separation channel 28 can be detected by the external detector.

In this case, a speed of scanning the light for the other ends 56*b* of respective of the light leading optical waveguides 56 is set to be sufficiently higher as compared with the moving speed of the sample through the separation channel 28. The speed of scanning the light can be determined to be higher than or equal to 1 m/sec–10 m/sec. For instance, since the moving speed of the sample flowing through the separation channel 28 is on the order of 100 μm/sec, even if the speed of scanning the light is set to be 1 m/sec, the scanning speed is sufficiently higher than the moving speed of the sample in the separation channel 28. It is therefore possible to detect where the sample is within the separation channel 28. When the light emitted from the external light source is scanned for one time under this condition, the lights which are received from the end section 58*a* of the light receiving optical waveguide 58 can be treated to be the lights measured at the substantially same time. It is therefore possible to detect a separation pattern of the sample which moves in the separation channel 28 by scanning the light emitted from the external light source for one time.

It is also possible to detect the moving speeds of the respective of the separated samples by scanning the light emitted from the external light source with a predetermined time interval, and then measuring the intensity of the light passing through the samples. Also, since the moving speeds of the compositions contained in the sample can be detected, it is possible to detect the respective compositions contained in the sample in higher precision based upon the moving speeds. For example, it is possible to detect the respective compositions by supplying a reference substance as well as the sample and then comparing a moving speed of the reference substance with the moving speeds of the respective compositions.

Figure 8A:
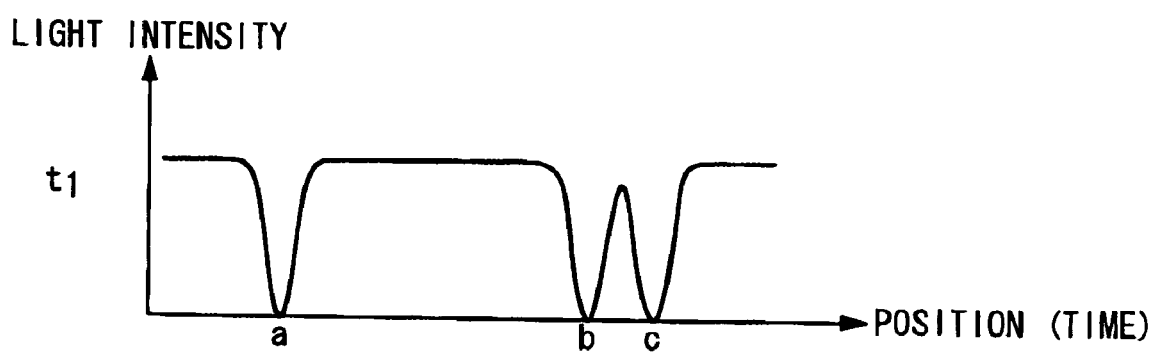
FIGS. 8A and 8B are diagram for representing intensity of light come out from a light receiving optical waveguide in the fourth embodiment of the present invention.
Figure 8B:
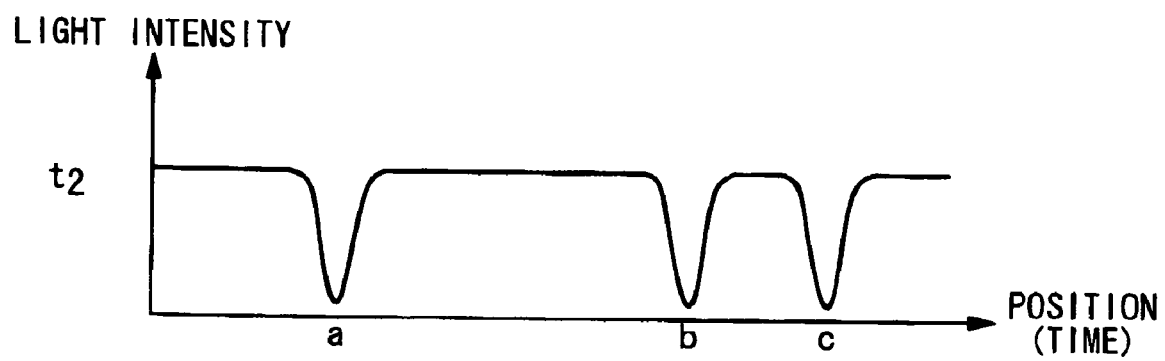

FIGS. 8A and 8B are diagrams showing intensities of outputted lights which are obtained when the light is sequentially supplied to the other ends 56*b* of respective of the light leading optical waveguides 56 by scanning the light emitted from the external light source. In FIGS. 8A and 8B, a time t1 and a time t2 after a predetermined time has elapsed from the time t1 are employed as starting times, respectively. In the drawings, an ordinate indicates the intensity of light, and an abscissa indicates the irradiation position (time) of the light emitted from the external light source. With these drawings, it is possible to detect in substantially real time where the sample is located within the separation channel 28. In this case, for example, it is found that the compositions "a", "b", and "c" contained in the sample are separated within the separation channel 28 at the time t1. It is also found that an interval between the compositions "b" and "c" at the time t2 becomes wider than the interval between the compositions "b" and "c" at the time "t1." It is possible to detect the moving speeds of the respective compositions on the basis of the change in the positions of the respective compositions "a", "b", and "c" between the time "t1" and the time "t2", and the time interval between the time t1 and the time t2. According to the microchip 54 of the present embodiment, as described above, since the separation patterns of the sample flowing in the separation channel 28 and the moving speeds of the respective samples can be detected, it is possible to detect a timing of collecting the compositions of the samples under the separation process. In particular, even when an unknown sample is separated and collected, since the flow-out times of the respective compositions can be predicted, the target composition can be firmly collected. Also, the target substance can be identified in high precision.

As previously explained, according to the present embodiment, a function capable of detecting peak positions of the compositions of the sample under the separating process is realized, which is not realized according to the conventional technique.

Also, the microchip 54 may be alternatively configured as shown in FIG. 9. In FIG. 9, the microchip 54 includes a plurality of light receiving optical waveguides 59 which are provided opposite to the plurality of light leading optical waveguides 56 across the separation channel 28. The plurality of light receiving optical waveguides 59 are optically connected to a light receiving optical waveguide 58 at an end section located opposite to the region which is in contact to the separation channel 28. Also in this case, the light receiving optical waveguide 58 is formed in such a manner that the light can be received from the end section 58*a* in a similar manner to that of FIG. 7. As a result, the lights which are led through respective of the plurality of light leading optical waveguides 56 can be collected and outputted as one output light, as in the case shown in FIG. 7. It is therefore possible to detect a timing of collecting the compositions of the sample under the separating process. In particular, even when an unknown sample is separated and collected, since the flow-out times of the respective compositions can be predicted, the target composition can be firmly collected.

FIFTH EMBODIMENT

Figure 10A:
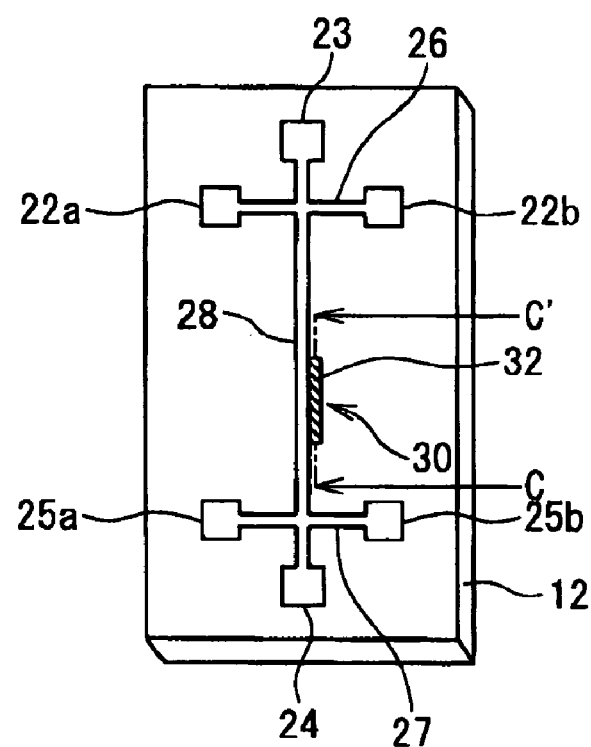
FIG. 10A is a cross sectional view for showing a structure of a microchip according to a fifth embodiment of the present invention.
Figure 10B:
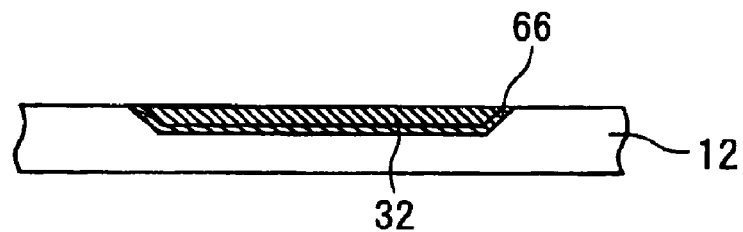
FIG. 10B is a cross sectional view along C–C' of the microchip in FIG. 10A.

FIG. 10A is a cross sectional view showing a structure of a microchip according to a fifth embodiment of the present invention. FIG. 10B is a cross sectional view of the microchip along C–C' in FIG. 10A.

In the above-described embodiment, the separation channel 28 of the microchip 10 is provided between the light leading optical waveguide 32a and the light receiving optical waveguide 32b. According to the present embodiment, as shown in FIG. 10A, the light leading optical waveguide 32a and the light receiving optical waveguide 32b are formed in an integral body as an optical waveguide 32, and the optical waveguide 32 is made to have a border with the separation channel 28.

Also, as shown in FIG. 10B, an edge section of the optical waveguide 32 is formed to be slope, and a reflective layer 66 can be formed on a surface of the end section. As a result, a light which is supplied from the upper direction of the substrate 12 can be led through the optical waveguide 32, and the light which propagates through the optical waveguide 32 can be outputted to the upper direction of the substrate 12.

In this case, when the light is led to the optical waveguide 32, an evanescent wave penetrates into the separation channel 28 at the region where the optical waveguide 32 has the border with the separation channel 28. By detecting an interaction between the evanescent wave and the sample flowing in the separation channel 28, it is possible to detect the compositions contained in the sample.

Figure 11A:
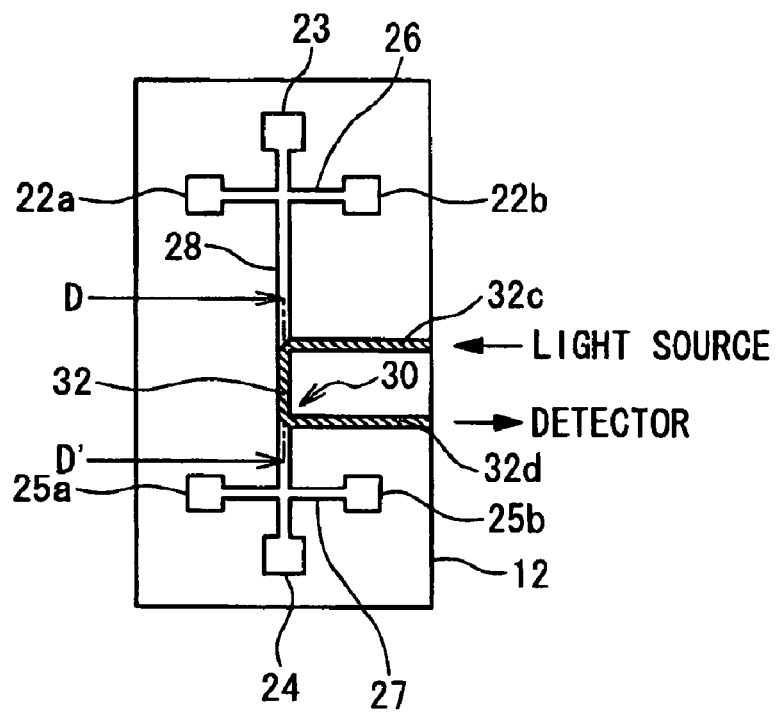
FIG. 11A is a cross sectional view for representing a structure of a modification of the microchip according to the fifth embodiment of the present invention.
Figure 11B:
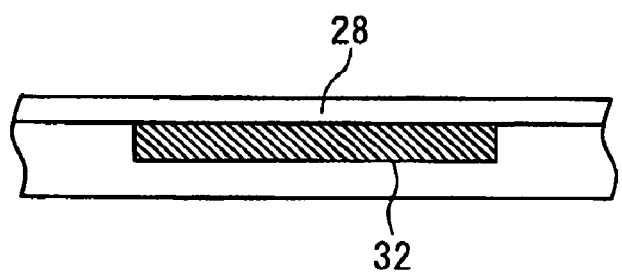
FIG. 11B is a cross sectional view along line D–D' of the microchip in FIG. 11A.

FIG. 11A is a cross sectional view showing a structure of a modification of the microchip according to this present embodiment. FIG. 11B is a cross sectional view for showing the microchip along D–D' in FIG. 11A.

Figure 11C:
FIG. 11C is a side view for representing the microchip in FIG. 11A.

According to the modification, as shown in FIG. 11B, the optical waveguide 32 is formed below the separation channel 28. In this case, a light is led from the side surface of the substrate 12 via a light leading optical waveguide 32c to the optical waveguide 32, and the light is come out from the side surface of the substrate 12 via a light receiving optical waveguide 32d. FIG. 11C is a diagram showing the side surface on which the light leading optical waveguide 32c and the light receiving optical waveguide 32d are formed. According to the present modification, when a light is led to the optical waveguide 32, an evanescent wave also penetrates into the separation channel 28 at the region where the optical waveguide 32 has the border with the separation channel 28. By detecting an interaction between the evanescent wave and the sample flowing in the separation channel 28, it is possible to detect the compositions contained in the sample.

Figure 12A:
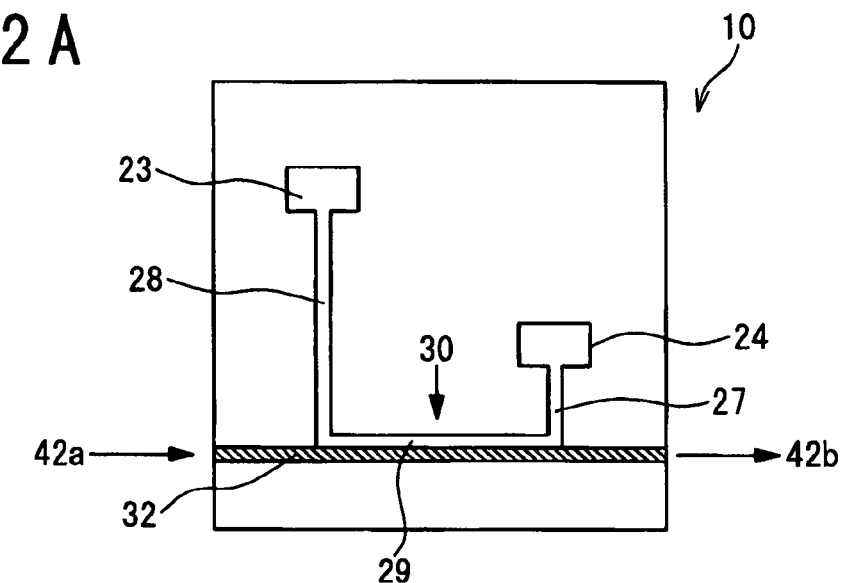
FIG. 12A is a cross sectional view for representing a structure of another modification of the microchip according to the fifth embodiment of the present invention.

FIG. 12A is a cross sectional view showing a structure of another modification of the microchip according to the present embodiment. The microchip 10 includes the separation channel 28, a collection channel 27, and a detection channel 29 which is provided between the separation channel 28 and the collection channel 27. The detection channel 29 is made with an angle with respect to the separation channel 28 and the collection channel 27. In the present modification example, a sample supplied to the liquid reservoir 23 is moved to the liquid reservoir 24 due to, for example, the capillary phenomenon and an application of a voltage. In this case, the sensing section 30 is provided in the detection channel 29.

Figure 12B:
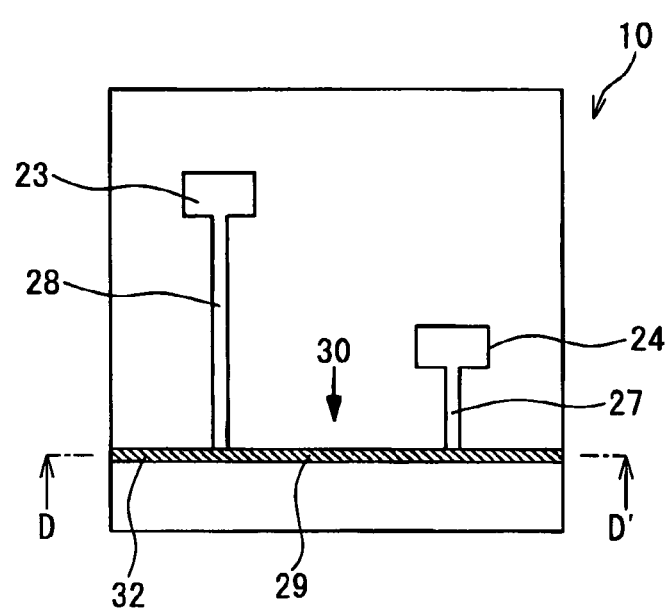
FIG. 12B is a cross sectional view for representing a structure of still another modification of the microchip according to the fifth embodiment of the present invention.
Figure 12C:
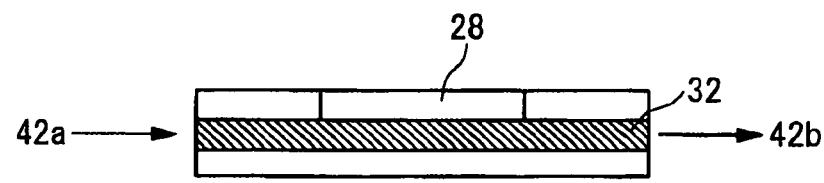
FIG. 12C is a cross sectional view along D–D' of the microchip in FIG. 12B.

As shown in FIG. 12A, the optical waveguide 32 is provided to have a border with the detection channel 29. Alternatively, as shown in FIG. 12B, the optical waveguide 32 can be formed below the detection channel 29. FIG. 12C is a cross sectional view for showing the microchip along D–D' shown in FIG. 12B. According to these modifications, when a light is led to the optical waveguide 32, an evanescent wave also penetrates into the separation channel 28 at the region where the optical waveguide 32 has the border with the separation channel 28. By detecting an interaction between the evanescent wave and the sample flowing in the separation channel 28, it is possible to detect the compositions contained in the sample.

SIXTH EMBODIMENT

Figure 13:
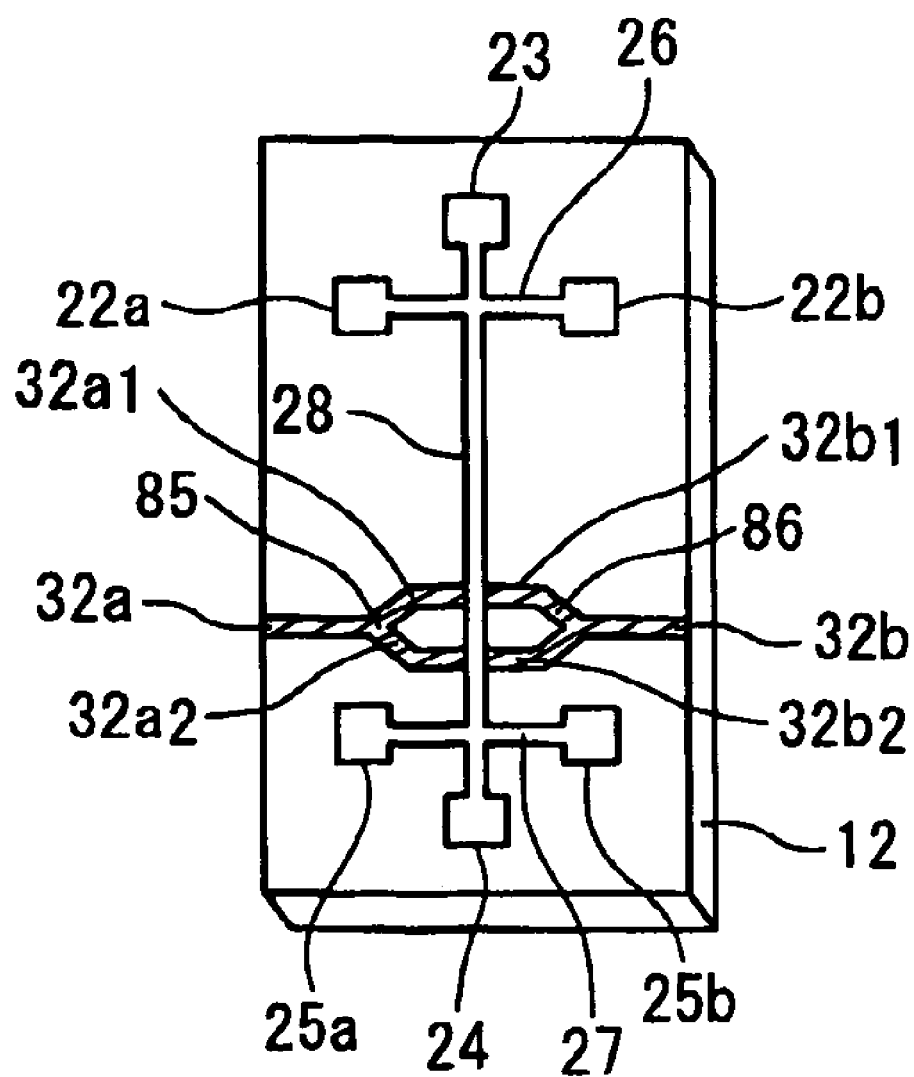
FIG. 13 is a cross sectional view for showing a structure of a microchip according to a sixth embodiment of the present invention.

FIG. 13 is a cross sectional view showing a structure of a microchip according to a sixth embodiment of the present invention. In this case, the light leading optical waveguide 32a is branched into a first light leading optical waveguide 32a1 and a second light leading optical waveguide 32a2 at a branching portion 85 within the substrate. Also, the light receiving waveguide 32b is subdivided into a first light receiving optical waveguide 32b1 and a second light receiving optical waveguide 32b2, and both of the optical waveguides flow into each other at a joining portion 86 within the substrate. The separation channel 28 is provided to intersect with both the first and the second light leading optical waveguides 32a1 and 32a2, and both the first and the second light receiving optical waveguides 32b1 and 32b2. Similar to the optical waveguides in the third embodiment, the first light receiving optical waveguide 32b1 and the second light receiving optical waveguide 32b2 are associated with the first light leading optical waveguide 32a1 and the second light leading optical waveguide 32a2, respectively.

The optical waveguide which is arranged in the above-described manner functions as an interferometer on the microchip. A light entered to the light leading optical waveguide 32a is divided at the branching portion 85 into a first light which propagates through the first light leading optical waveguide 32a1 and a second light which propagates through the second light leading optical waveguide 32a2. Respective of the first light and the second light pass through the separation channel 28, and then are entered into the corresponding one of the first light receiving optical waveguide 32b1 and the second light receiving optical waveguide 32b2, respectively. The first light and the second light are superposed at the joining portion 86. The superposed light is transmitted via the light receiving optical waveguide 32b to the external detector.

A refractive index of a liquid into which a biological composition is dissolved is increased. As a result, when a light passes through such a liquid into which a biological composition is dissolved, a phase of the light is slightly shifted. Under a condition that the biological composition contained in the sample flowing through the separation channel 28 does not arrive at a region between the first light leading optical waveguide 32a1 and the first light receiving optical waveguide 32b1, the phase of the light which passes through the channel is not shifted. As a consequence, the light which is entered from the light leading optical waveguide 32a is come out from the light receiving optical waveguide 32b without any attenuation. When the biological composition arrives at any one of the first light leading optical waveguide 32a1 and the second light receiving optical waveguide 32b1, the phase of the light which passes through the channel is shifted. As a result, the light which is supplied from the light leading optical waveguide 32a is attenuated in the joining portion 86, and the light which is come out from the light receiving optical waveguide 32b is significantly weakened as compared with the supplied light. It is therefore possible to detect the arrival of the biological composition by measuring the intensity of the outputted light.

As in the third embodiment, after two optical waveguides which intersect with the separation channel 28 are provided, both the branching portion and the joining portion may be formed outside the microchip. In this case, there is a problem in that a detection error is produced due to a difference in temperature distributions on the microchip. However, as in the example described above, when a small-scale interference circuit is formed on the microchip, the influence caused by the difference in the temperature distributions on the microchip can be suppressed, and thus the detection can be carried out correctly. It is preferable that a dimension of the interference circuit is several millimeters in square. According to the present embodiment, it is possible to analyze the sample flowing through the channel in high precision, even in the case of the very fine microchip.

SEVENTH EMBODIMENT

Figure 14A:
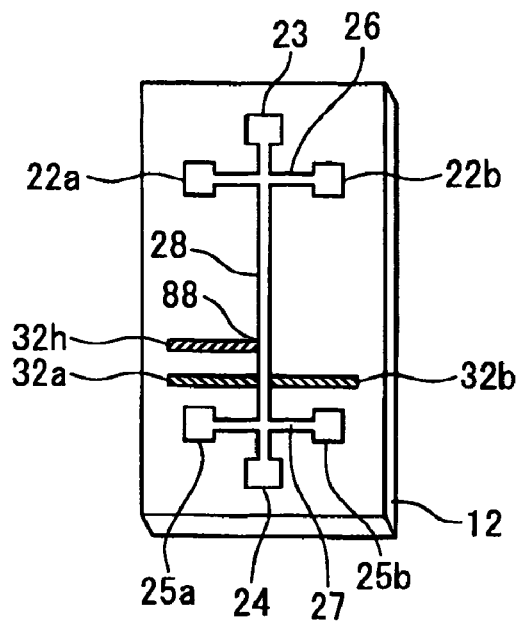
FIG. 14A is a cross sectional view for showing a structure of a microchip according to a seventh embodiment of the present invention.
Figure 14B:
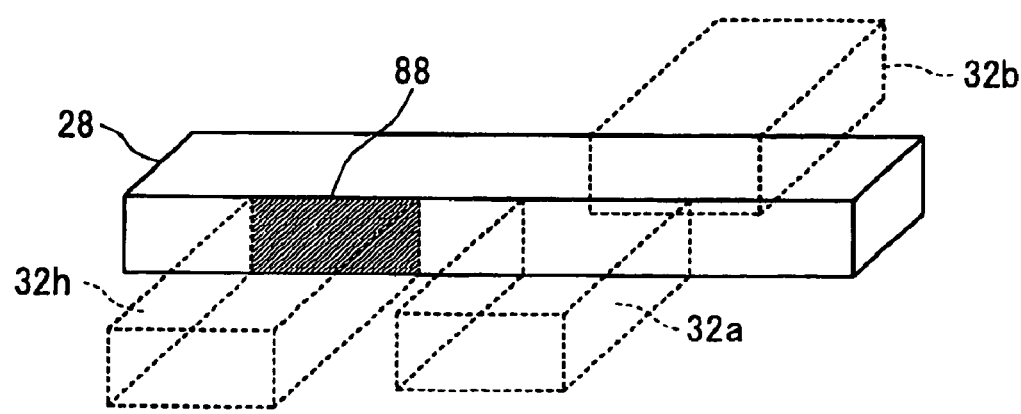
FIG. 14B is a diagram for showing a detailed structure of the microchip in FIG. 14A.

FIG. 14A is a cross sectional view showing a structure of a microchip according to a seventh embodiment of the present invention. In this case, in addition to the light leading optical waveguide 32a and the light receiving optical waveguide 32b, a heating optical waveguide 32h is formed to intersect with the separation channel 28. The heating optical waveguide 32h is formed upstream of the light leading optical waveguide 32a and the light receiving waveguide 32b with respect to the separation channel 28. FIG. 14B is a perspective view for showing the separation channel 28 and optical waveguides in the present embodiment. A plane 88 where the heating optical waveguide 32h intersects with the separation channel 28 is colored. It should be noted the heating optical waveguide 32h can be formed to have a border with the separation channel 28, or can be formed in such a way that the separation channel 28 is surrounded by the heating optical waveguide 32h.

The colored plane 88 is heated by a heating light which is entered in the heating optical waveguide 32h, and hence a sample which flows through the separation channel 28 is also heated. In other words, the heating optical waveguide 32h functions as a heater. As in the above-described embodiments, both the light leading optical waveguide 32a and the light receiving optical waveguide 32b are used for analyzing the sample. Since the heating optical waveguide 32h is formed upstream of the light leading optical waveguide 32a and the light receiving optical waveguide 32b, the sample can be heated before being optically analyzed.

It is known that a biochemical reaction related to enzyme which is utilized in clinical investigations proceeds most at approximately 38° C. Normally, a temperature of a channel is nearly equal to 25° C., i.e., a room temperature. Since a very small region of a microchip is heated, a biochemical reaction can be promoted and hence an efficiency of analyzing the sample can be improved.

In order to heat such a very small area of the microchip, it was necessary to provide a heating apparatus outside the microchip, or to provide an electric circuit (heater) within the microchip in addition to the optical waveguides used for an analysis purpose. However, according to the example mentioned above, the optical waveguide is employed as a heater, which can be formed in a similar manner to the optical waveguides used for the analysis. As a result, a heating apparatus is not required to be prepared outside the microchip. Furthermore, it is possible to omit additional steps for forming an electric circuit within the microchip. This apparatus makes it possible to analyze the sample in high precision with a short time by heating the sample up to the proper temperature before the analysis, without increasing the complexity of the structure of the microchip.

EIGHTH EMBODIMENT

Figure 15A:
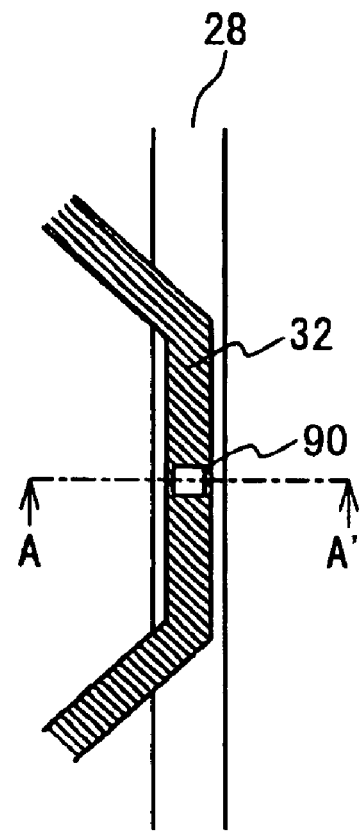
FIG. 15A is a schematic diagram for showing a microchip according to an eighth embodiment of the present invention.
Figure 15B:
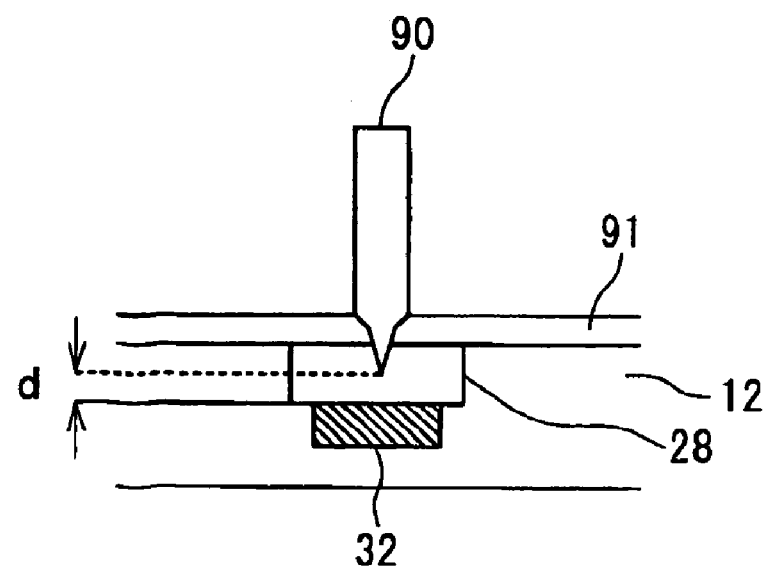
FIG. 15B is a cross sectional view along A–A' of the microchip in FIG. 15A.

FIG. 15A is a schematic diagram for showing a channel and an optical waveguide of a microchip according to an eighth embodiment of the present invention. FIG. 15B is a cross sectional view showing the microchip along A–A' in FIG. 15A.

An optical waveguide 32 is formed on a bottom surface of the separation channel 28, and a portion of the optical waveguide 32 is exposed to a bottom surface of the channel. A material having a larger refractive index than that of water is applied as the material of the optical waveguide 32. In this case, a total reflection can occur at a boundary plane between the optical waveguide 32 and a buffer of the separation channel 28. The surface of the portion of the optical waveguide 32 which is exposed to the separation channel 28 is formed to actively trap molecules. To that end, there are such means that no absorption preventing process may be applied or antibody molecules may be coated. A channel cover 91 is formed on the separation channel 28, and a near-field probe 90 is provided to penetrate through the channel cover 91. A tip portion of the near-field probe 90 reaches into the separation channel 28, and a distance measured from the bottom surface of the channel is equal to "d". The distance "d" is set to be 10 nm to approximately 50 nm. The structure of the near-field probe 90 is a general one.

As a method for detecting a sample by using a near-field light, a detecting method in a lighting mode and a detecting method in a collecting mode are possible.

According to the detecting method by way of the lighting mode, the near-field probe 90 is employed as a lighting, and a light having low intensity is led. When the light having the low intensity is led to the near-field probe 90, a near-field is generated at the tip portion of the near-field probe 90. As previously explained, the surface of the optical waveguide 32 which is exposed to the separation channel 28 is formed such that the surface can easily trap the biological molecules. As a result of an interaction between the near-field and the trapped biological molecules, a faint scattered light is generated. The scattered light is received by the optical waveguide 32, and then is detected at a light emitting portion of the optical waveguide 32. When the biological molecules are trapped on the surface of the portion of the optical waveguide 32 which is exposed to the separation channel 28, the intensity of the scattered light increases because the near-field at the tip portion of the near-field probe 90 comes close to the biological molecules which are dielectric substance. As a consequence, it is possible to detect the presence of the biological molecules.

According to the detecting method by way of the collecting mode, a light is led to the optical waveguide 32, and a high sensitivity detector (not shown) is provided at an output portion of the near-field probe 90. When the light is led to the optical waveguide 32, a near-field is formed also on the surfaces of the biological molecules which are trapped to the optical waveguide 32 exposed to the separation channel 28. As a result, a faint scattered light is generated in the vicinity of the tip portion of the near-field probe 90. The scattered light is detected by the high sensitivity detector. When the biological molecules are trapped on the portion of the optical waveguide 32 which is exposed to the separation channel 28, the intensity of the scattered light increases because the near-field comes close to the near-field probe 90. As a consequence, it is possible to detect the presence of the biological molecules.

In a normal absorptiometric analysis used for detecting the biological molecules, a sufficiently long optical length (longer than or equal to 100 μm) and sufficiently high molecular concentration (several hundreds of thousand molecules/ml) are required. When the size of the channel becomes smaller and the concentration of biological molecules decreases in accordance with higher integration of a biochip and less amount of samples, there is no means for detecting the biological molecules within the channels. According to the present embodiment, it is possible to detect the biological molecules within the channel, even when the channel size is small (smaller than or equal to 1 μm) and the concentration of the biological molecules is decreased (several hundreds of molecules/ml). Even in an extremely small channel, compositions contained in the sample can be optically detected.

NINTH EMBODIMENT

Figure 16:
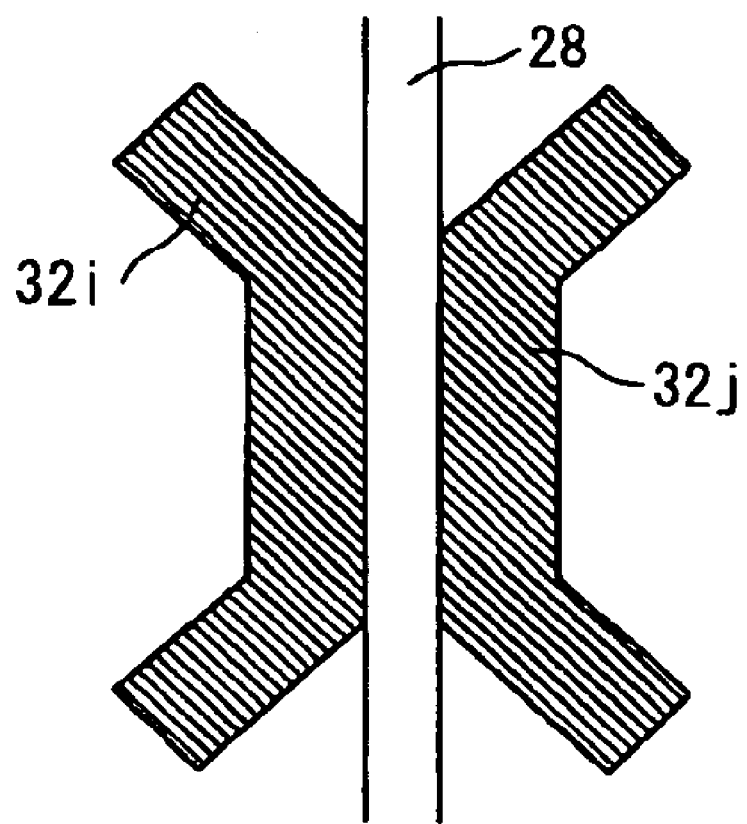
FIG. 16 is a cross sectional view for showing a structure of a microchip according to a ninth embodiment of the present invention.

FIG. 16 is a schematic diagram for representing structures of a channel and an optical waveguide of a microchip according to a ninth embodiment of the present invention. As in the eighth embodiment, samples can be detected by utilizing the near-field also in the present embodiment.

In the present embodiment, a separation channel 28 is very fine, and its width is smaller than or equal to 50 nm. Both of an optical waveguide 32$i$ and an optical waveguide 32$j$ are formed along the separation channel 28, and are arranged opposite to each other across the separation channel 28. In this case, the optical waveguides 32$i$ and 32$j$ are exposed to the separation channel 28 on the side of the separation channel 28. Also, as in the optical waveguide in the eighth embodiment, such a material having a larger refractive index than that of water is applied as the materials of the optical waveguides 32$i$ and 32$j$. As a result, a total reflection can occur at boundary surfaces between the optical waveguide 32$i$/32$j$ and a buffer of the separation channel 28. Widths of the optical waveguides 32$i$ and 32$j$ may be set to 5 μm–100 μm.

When a light is led to one optical waveguide 32$i$, a near-field is generated at the surface on the side of the separation channel 28. At this time, since the width of the separation channel 28 is very narrow to the same extent as the sizes of biological molecules which flow through the separation channel 28, the near-field can interact with the biological molecules when the biological molecules merely pass through the separation channel 28 even though the biological molecules are not trapped to the surface of the optical waveguide. When the near-field and the biological molecules contained in the sample interact with each other, a faint scattered light is generated. The scattered light is detected by a high sensitivity photodetector (not shown) through the other optical waveguide 32$j$. According to the present embodiment, it is possible to optically detect the compositions contained in the sample flowing through the extremely small channel can be optically detected, even in the simple microchip structure.

The present invention is described based upon the various embodiments. It should be noted that these embodiments are merely exemplified. It is therefore understood by a person who is skilled in the art that the combinations as to the respective components and the respective process operations can be modified in various ways, and such modifications are covered by the technical scope and spirit of the present invention.

Figure 22A:
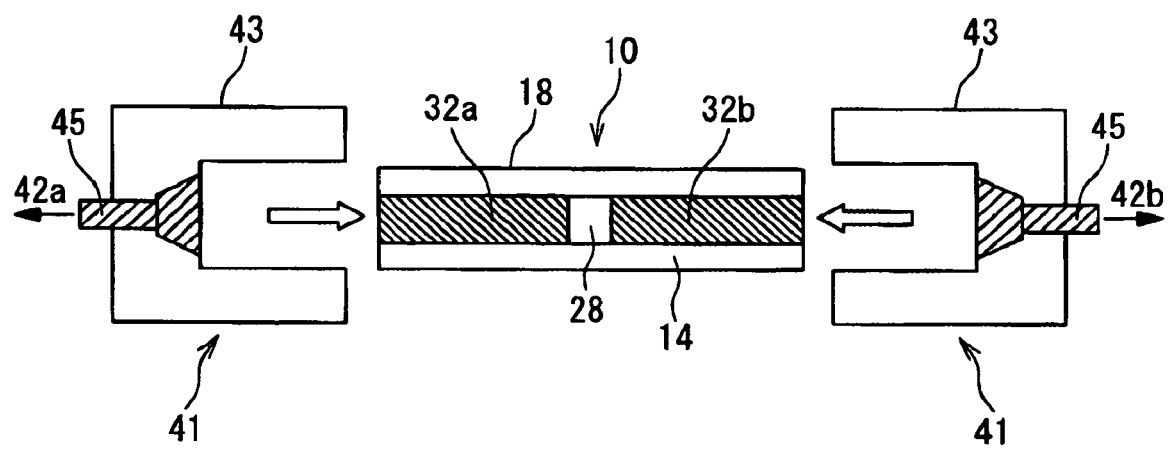
FIGS. 22A and 22B are diagrams for showing an example as to a connection between a microchip and an optical fiber.
Figure 22B:
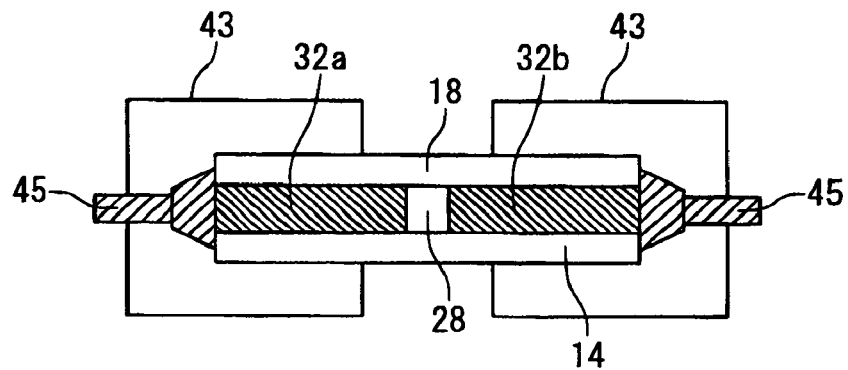
Figure 23A:
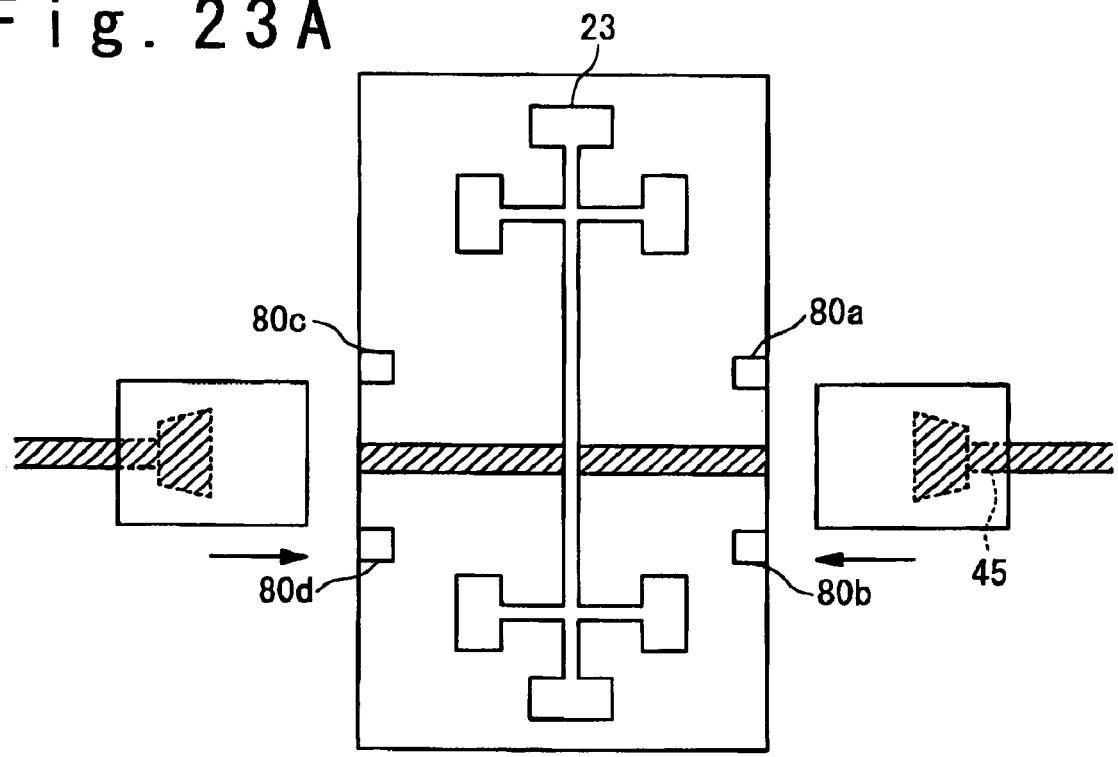
FIGS. 23A and 23B are top views of the microchip and the optical fiber shown in FIGS. 22A and 22B.
Figure 23B:
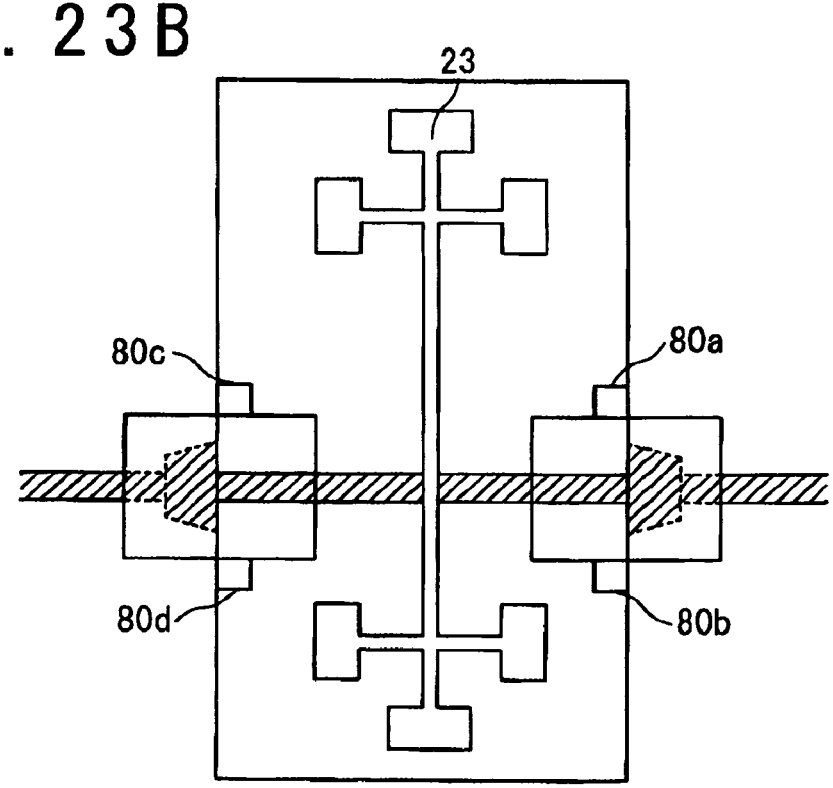

As shown in FIGS. 22A, 22B, 23A and 23B, the light leading optical waveguide 32$a$ and the light receiving optical waveguide 32$b$ can be configured to be connected to the light leading optical fiber 42$a$ and the light receiving optical fiber 42$b$ on the side surfaces thereof, respectively. FIG. 22A is a cross sectional view showing the side of both the microchip and connectors 41 which are used to connect the microchip. FIG. 22B is a diagram for representing such a condition that the microchip is connected with the connectors 41 shown in FIG. 22A. FIGS. 22B and 23B are top views for showing the structures shown in FIGS. 22A and 22B, respectively.

In this case, the light leading optical waveguide 32$a$ and the light receiving optical waveguide 32$b$ of the microchip 10 are connected via the connectors 41 to the light leading optical fiber 42$a$ and the light receiving optical fiber 42$b$, respectively. The connectors 41 include both clad layers 43 and core layers 45, and the clad layer 43 can be configured to include such concave portions which can accommodate thereinto the microchip 10. Also, the connectors 41 are formed in such a manner that when the microchip 10 is accommodated in the concave portions formed in the clad layers 43, both the light leading optical waveguide 32$a$ and the light receiving optical waveguide 32$b$ of the microchip 10 are connected to the core layers 45, respectively.

The connectors 41 and/or the substrate 12 are provided with positioning sections which are used for positioning the connectors 41 with respect to the substrate 12. Various sorts of structures may be conceived as the positioning portions. For instance, as indicated in FIGS. 23A and 23B, convex portions 80$a$, 80$b$, 80$c$, and 80$d$ can be formed on the substrate 12. Alternatively, convex portions can be formed on the connectors 41, and grooves which are engaged with the convex portions can be formed on the substrate 12. Also, a notch portion capable of accommodating the connector 41$a$ into a predetermined position can be formed on the cover member 20, and the connector 41 can be accommodated in the notch portion.

Such connectors 41 can be applied to all the microchips in all the embodiments described above.

Also, as previously explained in the fourth embodiment, the light emitted from the light source may be entered via the focusing lens, or may be directly entered to the light leading optical waveguide. Also, in the above-described embodiments, the light is transmitted from the light receiving optical waveguide via the optical fiber to the external detector. While the means for transmitting the light from the light receiving optical waveguide is not limited only to the optical fiber, this means may be alternatively arranged in such a manner that, for instance, the light may be directly detected by the detector, or may be transmitted via other means to the detector.

Also, the substrate where the optical waveguides are formed is not limited only to the one described in the embodiments, but also may be alternatively formed by various methods. For instance, in the case of quartz-series materials, a substrate can be manufactured based upon a low pressure CVD (LPCVD) method, a plasma CVD method, a flame deposition method, a vapor deposition method, a sputtering method, a sol-gel method, an ion diffusion method and the like.

Furthermore, according to the embodiments, the microchip has the separation channel 28 between the liquid reservoir 23 and the liquid reservoir 24. Alternatively, the microchip may include not only the separation channel but also other channels used for other purposes such as a channel used only for transporting samples and so on.

The invention claimed is:

1. A microchip comprising:
    a clad layer having a channel through which a sample flows; and
    at least one optical waveguide formed within said clad layer and having a higher refractive index than said clad layer,
    wherein said optical waveguide is formed to act on said channel optically.

2. The microchip according to claim 1,
    wherein a light led from one end of said optical waveguide passes through said channel and comes out from another end of said optical waveguide.

3. The microchip according to claim 2,
    wherein said channel is formed to divide said optical waveguide.

4. The microchip according to claim 2,
    wherein said at least one optical waveguide includes a plurality of optical waveguides, and
    said plurality of optical waveguides are formed apart from each other in said clad layer.

5. The microchip according to claim 2,
    wherein said one end and said another end of said optical waveguide are formed wider than another region of said optical waveguide.

6. The microchip according to claim 2,
    wherein said optical waveguide is formed wider at a boundary between said optical waveguide and said channel than another region of said optical waveguide.

7. The microchip according to claim 1,
    wherein said at least one optical waveguide includes a plurality of optical waveguides,
    said plurality of optical waveguides are formed within said clad layer, said plurality of optical waveguides including: a plurality of light leading optical waveguides; and a light receiving optical waveguide,
    said channel is formed between said plurality of light leading optical waveguides and said light receiving optical waveguide,
    said plurality of light leading optical waveguides are formed to lead a light at a plurality of different positions of said channel, and
    said light receiving optical waveguide is formed to receive and output said light passing through said plurality of different positions.

8. The microchip according to claim 7,
    wherein said plurality of light leading optical waveguides are formed apart from each other and substantially perpendicular to said channel.

9. The microchip according to claim 7,
    wherein said light receiving optical waveguide is formed along said channel.

10. The microchip according to claim 1,
    wherein said at least one optical waveguide includes a plurality of optical waveguides,
    said plurality of optical waveguides are formed within said clad layer, said plurality of optical waveguides including: a plurality of light leading optical waveguides; a plurality of first light receiving optical waveguides as many as said plurality of light leading optical waveguides; and a second light receiving optical waveguide,
    said channel is formed between said plurality of light leading optical waveguides and said plurality of first light receiving optical waveguides,
    said plurality of light leading optical waveguides are formed to lead a light at a plurality of different positions of said channel,
    each of said plurality of first light receiving optical waveguides is formed to receive said light passing through corresponding one of said plurality of different positions, and
    said second light receiving optical waveguide is formed to receive and output said light propagating through each of said plurality of first light receiving optical waveguides.

11. The microchip according to claim 10,
    wherein said plurality of light leading optical waveguides are formed apart from each other and substantially perpendicular to said channel, and
    said plurality of first light receiving optical waveguides are formed apart from each other and substantially perpendicular to said channel.

12. The microchip according to claim 10,
    wherein said second light receiving optical waveguide is formed along said channel.

13. The microchip according to claim 1,
    wherein said optical waveguide is formed to share a border with said channel.

14. The microchip according to claim 13,
    wherein said optical waveguide includes:
    a region having a border with said channel;
    a light leading optical waveguide connected to said region and leading a light to said region; and
    a light receiving optical waveguide connected to said region, and receiving and outputting said light propagating through said region.

15. The microchip according to claim 13,
    wherein said channel includes:
    a separation region for separating said sample; and
    a detection region connected to said separation region and formed with an angle with respect to said separation region,
    wherein said optical waveguide shares a border with said detection region.

16. The microchip according to claim 1,
    wherein said optical waveguide has:
    a light leading optical waveguide for leading a light to said channel which branches into a first light leading optical waveguide and a second light leading optical waveguide in said clad layer;
    a light receiving optical waveguide for receiving said light passing through said channel which branches into a first light receiving optical waveguide and a second light receiving optical waveguide in said clad layer,
    wherein said channel is formed to pass through between said first light leading optical waveguide and said first light receiving optical waveguide and between said second light leading optical waveguide and said second light receiving optical waveguide, a first light led from said first light leading optical waveguide to said channel enters into said first light receiving optical waveguide, a second light led from said second light leading optical waveguide to said channel enters into said second light receiving optical waveguide, and said first light and said second light are superposed in said light receiving optical waveguide.

17. The microchip according to claim 1,
wherein said optical waveguide has:
a light leading optical waveguide for leading a light to said channel;
a light receiving optical waveguide for receiving and outputting said light passing through said channel; and
a heating optical waveguide formed upstream of said light leading optical waveguide with respect to said channel,
wherein a boundary surface is formed between said heating optical waveguide and said channel, and
said boundary surface is colored.

18. The microchip according to claim 1, further comprising a near-field probe whose tip reaches within said channel,
wherein said optical waveguide is formed along said channel, and is exposed to said channel at a region facing said tip of said near-field probe.

19. The microchip according to claim 18,
wherein a surface of said optical waveguide is processed to trap at least one molecule in said sample.

20. The microchip according to claim 1,
wherein said optical waveguide includes:
a first optical waveguide along said channel which has a surface exposed to said channel;
a second optical waveguide along said channel which has a surface exposed to said channel,
wherein said channel is formed between said first optical waveguide and said second optical waveguide, and a width of said channel is comparative to molecule in said sample.

21. The microchip according to claim 20,
wherein said width of channel is no more than 50 nm.

22. The microchip according to claim 1,
wherein said optical waveguide is formed to be connectable with an optical fiber at an end section which does not act on said channel optically.

23. The microchip according to claim 22,
wherein said end section of said optical waveguide forms a slope.

24. The microchip according to claim 1,
wherein said channel is a groove formed on said clad layer.

25. A method of manufacturing a microchip comprising:
(a) forming a lower clad layer on a base substrate;
(b) forming at least one groove on said lower clad layer;
(c) forming an optical waveguide in said groove, said optical waveguide having a higher refractive index than said lower clad layer;
(d) forming an upper clad layer over said lower clad layer to cover said optical waveguide, said upper clad layer having a lower refractive index than said optical waveguide; and
(e) forming a channel to act on said optical waveguide optically;
wherein said groove forming includes forming a reflective layer on a surface of said groove.

26. The method of manufacturing a microchip according to claim 25,
wherein said channel forming includes forming said channel to intersect with said optical waveguide.

27. The method of manufacturing a microchip according to claim 25,
wherein said channel forming includes forming said channel to divide said optical waveguide.

28. The method of manufacturing a microchip according to claim 25,
wherein said channel forming includes forming said channel to share a border with said optical waveguide.

29. The method of manufacturing a microchip according to claim 25,
wherein said groove forming includes forming an end section of said groove to be a slope.

30. The method of manufacturing a microchip according to claim 25,
wherein said upper clad layer forming includes forming said upper clad layer which has a substantially equal refractive index to that of said lower clad layer.

31. A method of detecting compositions by using a microchip including a clad layer having a channel, and a plurality of light leading optical waveguides and a plurality of light receiving optical waveguides which are formed in said clad layer to intersect with said channel, comprising:
(A) flowing a sample in said channel;
(B) inputting a light to a plurality of positions of said channel almost simultaneously through said plurality of light leading optical waveguides;
(C) said light passing through said sample at said plurality of positions;
(D) receiving through respective of said plurality of light receiving optical waveguides said light passing through said plurality of positions; and
E) analyzing said sample flowing in said channel based on properties of said received light.

32. The method of detecting compositions according to claim 31,
wherein said analyzing includes analyzing said sample at said plurality of positions almost simultaneously.

33. The method of detecting compositions according to claim 31,
wherein said inputting and said receiving are repeated for a plurality of times at a predetermined interval, and
a speed of travel of said sample along said channel is detected in said analyzing based on said plurality of positions and said predetermined interval.

34. A method of detecting compositions by using a microchip including a clad layer having a channel, a plurality of light leading optical waveguides formed in said clad layer to intersect with said channel, and a light receiving optical waveguide formed along said channel in said clad layer, comprising:
(F) flowing a sample in said channel;
(G) inputting a light to a plurality of positions of said channel sequentially by using said plurality of light leading optical waveguides;
(H) said light passing through said sample at said plurality of positions;
(I) receiving through respective of said plurality of light receiving optical waveguides sequentially said light passing through said plurality of positions; and
(J) analyzing said sample flowing in said channel based on properties of said received light.

35. The method of detecting compositions according to claim 34, wherein said inputting includes scanning said light at a speed larger than a speed of said sample flowing through said channel.

36. The method of detecting compositions according to claim 34,
wherein said inputting and said receiving are repeated for a plurality of times at a predetermined interval, and
a speed of travel of said sample along said channel is detected in said analyzing based on said plurality of positions and said predetermined interval.

37. The method of detecting compositions according to claim 33, further comprising:
predicting a timing of collecting said sample based on said speed of travel of said sample.

38. A method of detecting compositions by using a microchip including a clad layer having a channel and an optical waveguide formed in said clad layer to share a border with said channel, comprising:
(K) flowing a sample in said channel;
(L) inputting a light from one end of said optical waveguide;
(M) an interaction between an evanescent wave of said light and said sample occurring at a region where said optical waveguide is in contact with said channel;
(N) receiving said light from another end said optical waveguide; and
(O) analyzing said sample flowing in said channel based on properties of said received light.

39. A method of detecting compositions by using a microchip including a clad layer having a channel, a light leading optical waveguide which is formed in said clad layer and branches into a first light leading optical waveguide and a second light leading optical waveguide intersecting with said channel, and a light receiving optical waveguide which is formed in said clad layer and branches into a first light receiving optical waveguide and a second light receiving optical waveguide intersecting with said channel, comprising:
(P) flowing a sample in said channel;
(Q) dividing a light led from said light leading optical waveguide into a first eight propagating in said first light leading optical waveguide and a second light propagating in said second light leading optical waveguide;
(R) leading said first light to said channel through said first light leading optical waveguide;
(S) leading said second eight to said channel through said second light leading optical waveguide;
(T) receiving said first light passing through said channel by said first light receiving optical waveguide;
(U) receiving said second light passing through said channel by said second light receiving optical waveguide;
(V) superposing said first light and said second light in said light receiving optical waveguide; and
(W) analyzing said sample flowing in said channel based on properties of said superposed light.

40. A method of detecting compositions by using a microchip including a clad layer having a channel, a light leading optical waveguide and a light receiving optical waveguide formed in said clad layer to intersect with said channel, and a heating optical waveguide having a border surface with respect to said channel, in which said heating optical waveguide is formed upstream of said light leading optical waveguide with respect to said channel and said border surface is colored, comprising:
(AA) flowing a sample in said channel;
(BB) leading a heating light to said heating optical waveguide;
(CC) heating said border surface between said heating optical waveguide and said channel by said heating light;
(DD) heating said sample which is in contact with said heated border surface;
(EE) a light led to said light leading optical waveguide passing through said heated sample;
(FF) receiving said light through said light receiving optical waveguide; and
(GG) analyzing said sample flowing in said channel based on properties of said received light.

41. A method of detecting compositions by using a microchip including a clad layer having a channel, an optical waveguide formed in said clad layer along said channel, and a near-field prove whose tip reaches within said channel, in which said optical waveguide is exposed to said channel at a region facing said tip of said near-field probe, comprising:
(HH) flowing a sample in said channel;
(II) leading a light to said near-field probe;
(JJ) generating a near-field adjacent to said tip of said near-field probe;
(KK) generating a scattered light by an interaction between said near-field and said sample;
(LL) receiving said scattered light by said optical waveguide; and
(MM) analyzing said sample flowing in said channel based on properties of said received scattered light.

42. A method of detecting compositions by using a microchip including a clad layer having a channel, and a first optical waveguide and a second optical waveguide which are formed in said clad layer along said channel and have surfaces exposed to said channel, comprising:
(NN) flowing a sample in said channel;
(OO) leading a light to said first optical waveguide;
(PP) generating a near-field adjacent to said surface of said first optical waveguide exposed to said channel;
(QQ) generating a scattered light by an interaction between said near-field and said sample;
(RR) receiving said scattered light by said second optical waveguide; and
(SS) analyzing said sample flowing in said channel based on properties of said received scattered light.

* * * * *